United States Patent [19]

Kawabata et al.

[11] Patent Number: 5,322,639
[45] Date of Patent: Jun. 21, 1994

[54] CARBOXYLIC ACID ESTER COMPOUND, LIQUID CRYSTAL MATERIAL, LIQUID CRYSTAL COMPOSITION AND LIQUID CRYSTAL ELEMENT

[75] Inventors: Junichi Kawabata; Hideo Yamaoka; Yuuichirou Tatsuki; Shinichi Nishiyama, all of Sodegaura, Japan

[73] Assignee: Mitsui Petrochemical Industries, Ltd., Tokyo, Japan

[21] Appl. No.: 45,787

[22] Filed: Apr. 14, 1993

[30] Foreign Application Priority Data

Apr. 14, 1992 [JP] Japan ................... 4-094462

[51] Int. Cl.$^5$ ............... C09K 19/32; C09K 19/52; C07C 69/74; G02F 1/13
[52] U.S. Cl. .................. 252/299.62; 252/299.01; 252/299.64; 252/299.65; 252/299.66; 252/299.67; 560/127; 560/138; 359/103
[58] Field of Search ............... 252/299.01, 299.61, 252/299.62, 299.63, 299.66, 299.67; 359/103; 560/127, 139

[56] References Cited

U.S. PATENT DOCUMENTS 4,846,998 7/1989 Pohl et al. ................ 252/299.63
4,985,583 1/1991 Eidenschink et al. ......... 252/299.01
5,246,622 9/1993 Shimizu et al. ............. 252/299.62

FOREIGN PATENT DOCUMENTS 0205340 12/1986 European Pat. Off. .

Primary Examiner—Shean Wu
Attorney, Agent, or Firm—Sherman and Shalloway

[57] ABSTRACT

The carboxylic acid ester compound of the invention is represented by the following formula [I]:

$$R-COO-A^1-Y^1-A^2-(Y^2-A^3)_n-COO-\overset{Q^1}{\underset{|}{C^*H}}-(CH_2)_q-CH_3 \quad [I]$$

wherein R is an alkyl group of 3-20 carbon atoms; n is 0 or 1; at least one of $A^1$, $A^2$ and $A^3$ is a group having tetralin structure, and the residual groups of $A^1$, $A^2$ and $A^3$ are each independently a group having specific aromatic cyclic structure such as a phenylene group and a biphenyl group; $Y^1$ and $Y^2$ are each independently a group selected from the group consisting of —COO—, —CH$_2$CH$_2$— and —CH$_2$O—; $Q^1$ is a group selected from the group consisting of —CH$_3$, —CF$_3$, —C$_2$H$_5$ and —C$_2$F$_5$; and q is an integer of 4 to 12.

This carboxylic acid ester compound may be used as an antiferroelectric liquid crystal material, and also be used as a liquid crystal composition by using other liquid crystal material in combination. A liquid crystal element which is formed by filling the carboxylic acid ester compound in a gap between two substrates opposite to each other shows excellent properties required for antiferroelectric liquid crystal elements, for example, high speed switching.

9 Claims, 8 Drawing Sheets

CARBOXYLIC ACID ESTER COMPOUND, LIQUID CRYSTAL MATERIAL, LIQUID CRYSTAL COMPOSITION AND LIQUID CRYSTAL ELEMENT

FIELD OF THE INVENTION

The present invention relates to a novel carboxylic acid ester (carboxylate) compound, a liquid crystal material comprising the compound, a liquid crystal composition comprising the compound and a liquid crystal compound other than the carboxylic acid ester, and a liquid crystal element using the liquid crystal material or the composition.

BACKGROUND OF THE INVENTION

Display devices using liquid crystal compounds, which are used widely at present, are driven in a TN (twisted nematic) mode.

Such driving display devices, however, have problems that since the position of the molecule of the liquid crystal compound present in the element must be changed in order to change displayed images, the driving time necessary therefor is prolonged, and also a voltage necessary for changing the position of the molecule of the liquid crystal compound becomes higher and electric power consumption becomes larger.

Differing from switching elements utilizing the TN mode or a STN mode, switching elements comprising ferroelectric liquid crystal compounds are able to function as switching elements only by changing the direction of molecular orientation of the liquid crystal compounds, and hence the switching time required for operating the switching elements is prominently shortened. Further, because a Ps×E value obtained from a spontaneous polarization (Ps) of the ferroelectric liquid crystal compound and an intensity of the electric field (E) applied thereto is an effective energy output for changing the direction of molecular orientation of the liquid crystal compound, the electric power consumption required therefor can also be extremely reduced. Such ferroelectric liquid crystal compounds are suitable particularly for use in display devices for moving picture, because they have two stable states depending upon the direction of the applied electric field, namely, bi-stability, and also have very favorable switching threshold value characteristics.

When such ferroelectric liquid crystal compounds are used in optical switching elements or the like, these compounds are required to have various characteristics such that an operating temperature is in the vicinity of or below ordinary temperature, an operating temperature range is broad, a switching speed is high (fast), and a switching threshold value voltage is within an appropriate range. In particular, of these characteristics, the operating temperature range is especially important when the ferroelectric crystal compounds are put into practical use.

However, in ferroelectric liquid crystal compounds known hitherto, the operating temperature range is generally narrow, and even in the case of ferroelectric liquid crystal compounds having a wide operating temperature range, the operating temperature range is in a high temperature region out of room temperature, as described, for example, in a paper by R. B. Meyer et al., "J. de Phys.", Vol. 36, p. L-69 (1975) or in a paper by M. Taguchi and T. Harada, "Proceedings of Eleventh Conference on Liquid Crystal," p. 168 (1985). Thus, no ferroelectric liquid crystal compounds satisfactory from the standpoint of practical use are obtainable yet.

OBJECT OF THE INVENTION

An object of the present invention is to provide a novel carboxylate compound and a liquid crystal material comprising the novel carboxylate compound. In particular, the object of the invention is to provide a novel carboxylate compound capable of forming a liquid crystal element having excellent properties such as wide operating temperature range, high switching speed, prominently reduced electric power consumption and stable contrast, and uses of the carboxylate compound.

SUMMARY OF THE INVENTION

The carboxylic acid ester (carboxylate) compound of the invention is represented by the following formula [I]:

$$R-COO-A^1-Y^1-A^2-(Y^2-A^3)_n-COO-C^*H-(CH_2)_q-CH_3 \quad \text{[I]}$$
$$\qquad\qquad\qquad\qquad\qquad\qquad\qquad\qquad\qquad\quad |$$
$$\qquad\qquad\qquad\qquad\qquad\qquad\qquad\qquad\qquad\ Q^1$$

wherein R is an alkyl group of 3-20 carbon atoms, n is 0 or 1, at least one of $A^1$, $A^2$ and $A^3$ is

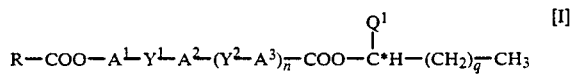

and the residual $A^1$, $A^2$ and $A^3$ are each independently a member selected from the group consisting of

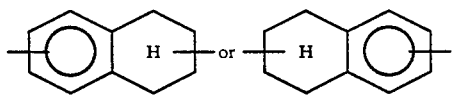

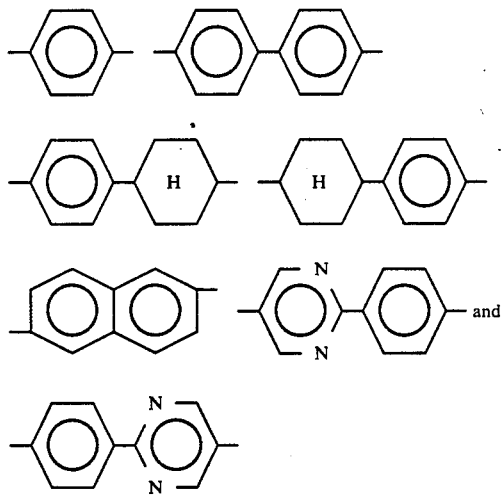

$Y^1$ and $Y^2$ are each independently a member selected from the group consisting of $-COO-$, $-CH_2CH_2-$ and $-CH_2O-$, $Q^1$ is a member selected from the group consisting of $-CH_3$, $-CF_3$, $-C_2H_5$ and $-C_2F_5$, and q is an integer of 4 to 12.

The liquid crystal material of the invention comprises the carboxylate compound represented by the above formula [I].

The liquid crystal composition of the invention comprises the carboxylate compound represented by the above formula [I] and a liquid crystal compound other than the carboxylate compound.

The liquid crystal element of the invention comprises a cell and a liquid crystal material or composition, said cell comprising two substrates facing to each other and a gap formed by the substrates, said liquid crystal material or composition being filled in the gap, wherein the liquid crystal material or composition comprises the carboxylate compound represented by the above formula [I].

According to the present invention, a novel carboxylate compound is provided. The carboxylate compound is very useful as a liquid crystal material. Therefore, a liquid crystal composition comprising this carboxylate compound shows excellent liquid crystal characteristics. A liquid crystal element comprising the liquid crystal material or the liquid crystal composition also shows excellent liquid crystal characteristics.

By the use of the carboxylate compound of the invention as a liquid crystal material, there can be obtained various kinds of devices having excellent characteristics such as wide operating temperature range, high switching speed, very small electric power consumption and stable high contrast.

DETAILED DESCRIPTION OF THE INVENTION

Figure 1:
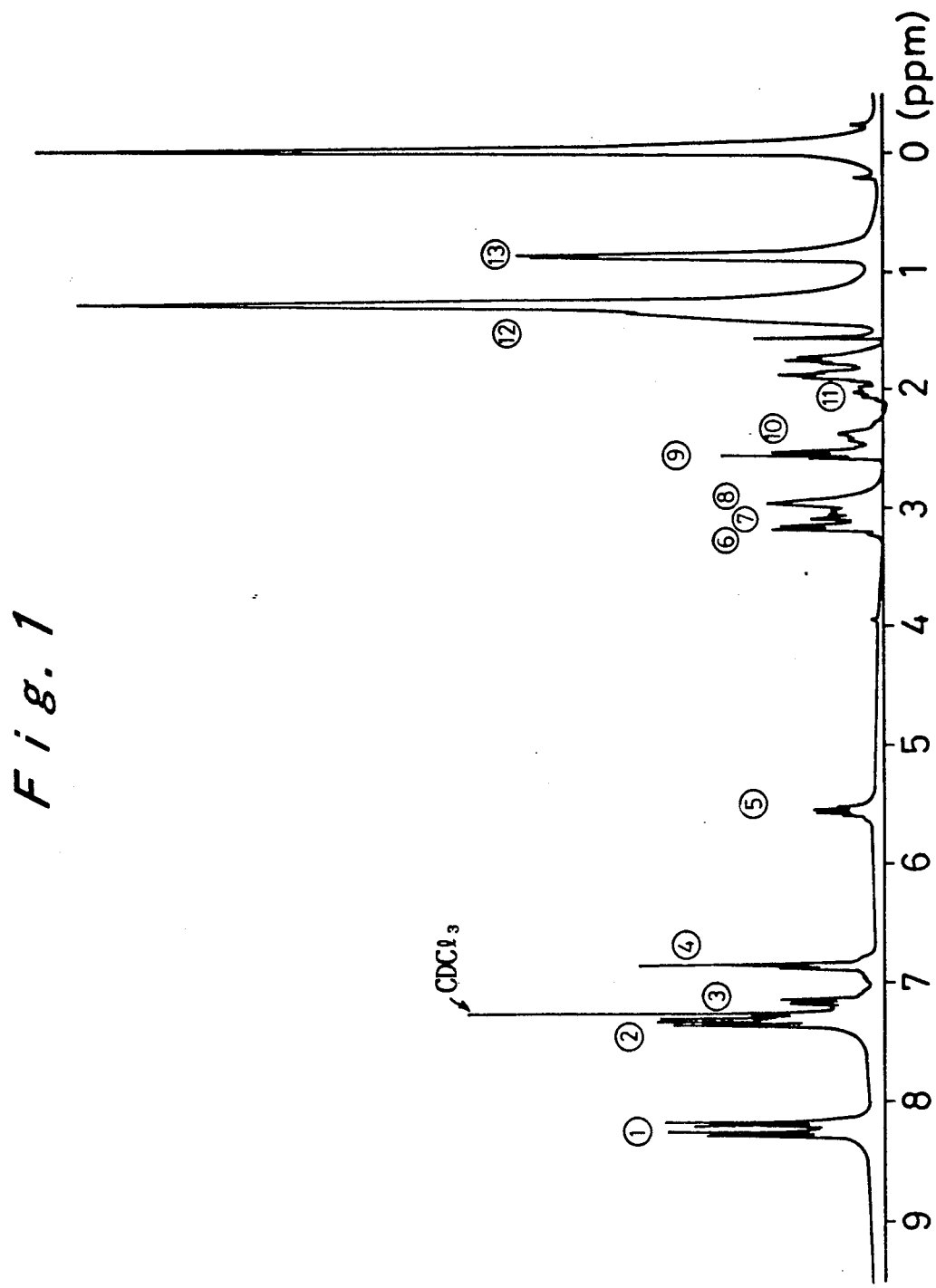
FIG. 1 shows a $^1$H-NMR spectrum of 6-(4'-decanoyloxybiphenyl-4''-carbonyloxy)-1,2,3,4-tetrahydronaphthalene-2-carboxylic acid R-1'''-trifluoromethylheptyl ester [Exemplified Compound (31)].

The present invention is described below in detail.

First, the carboxylate compound and the liquid crystal material of the invention are described.

The carboxylate compound of the invention is represented by the following formula [I].

The liquid crystal material of the invention comprises the carboxylate compound represented by the above formula [I].

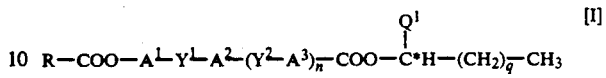

In the above formula [I], R is an alkyl group of 3-20 carbon atoms.

The alkyl group may be any of straight chain, branched chain and alicyclic forms. In particular, the carboxylate compound having a straight chain alkyl group as R exhibits excellent liquid crystal properties because the molecule has a rigid linear structure. Concrete examples of the straight chain alkyl groups include hexyl group, heptyl group, octyl group, nonyl group, decyl group, undecyl group, dodecyl group, tetradecyl group, hexadecyl group and octadecyl group.

In the above formula [I], n is 0 or 1. Accordingly, when n is 0, none of $Y^2$ and $A^3$ are present in the formula [I].

Further, at least one of $A^1$, $A^2$ and $A^3$ which are present in the above formula [I] is a group represented by the following formula.

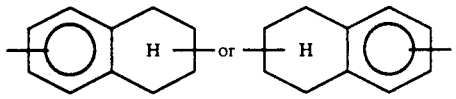

That is, when n is 0, at least one of $A^1$ and $A^2$ is required to be a group represented by the above formula. When n is 1, at least one of $A^1$, $A^2$ and $A^3$ is a group represented by the above formula, or all of $A^1$, $A^2$ and $A^3$ may be represented by the above formula.

Examples of the 1,2,3,4-tetrahydronaphthyl group include 1,2,3,4-tetrahydro-1,5-naphthyl group, 1,2,3,4-tetrahydro-1,6-naphthyl group, 1,2,3,4-tetrahydro-2,6-naphthyl group and 1,2,3,4-tetrahydro-1,7-naphthyl group.

For the use of the carboxylate compound of the invention as a liquid crystal compound (material), it is preferred that the molecule is linear as a whole. On that account, 1,2,3,4-tetrahydro-2,6-naphthyl group is particularly preferred as the 1,2,3,4-tetrahydronaphthyl group.

Also with respect to the 5,6,7,8-tetrahydronaphthyl group, 5,6,7,8-tetrahydro-2,6-naphthyl group is particularly preferred.

Examples of structures of the carboxylate compound represented by the formula [1] wherein $A^1$, $A^2$ and $A^3$ are the above-mentioned groups are given below. The following examples are those in which the tetrahydronaphthyl group is 1,2,3,4-tetrahydro-2,6-naphthyl group or 5,6,7,8-tetrahydro-2,6-naphthyl group.

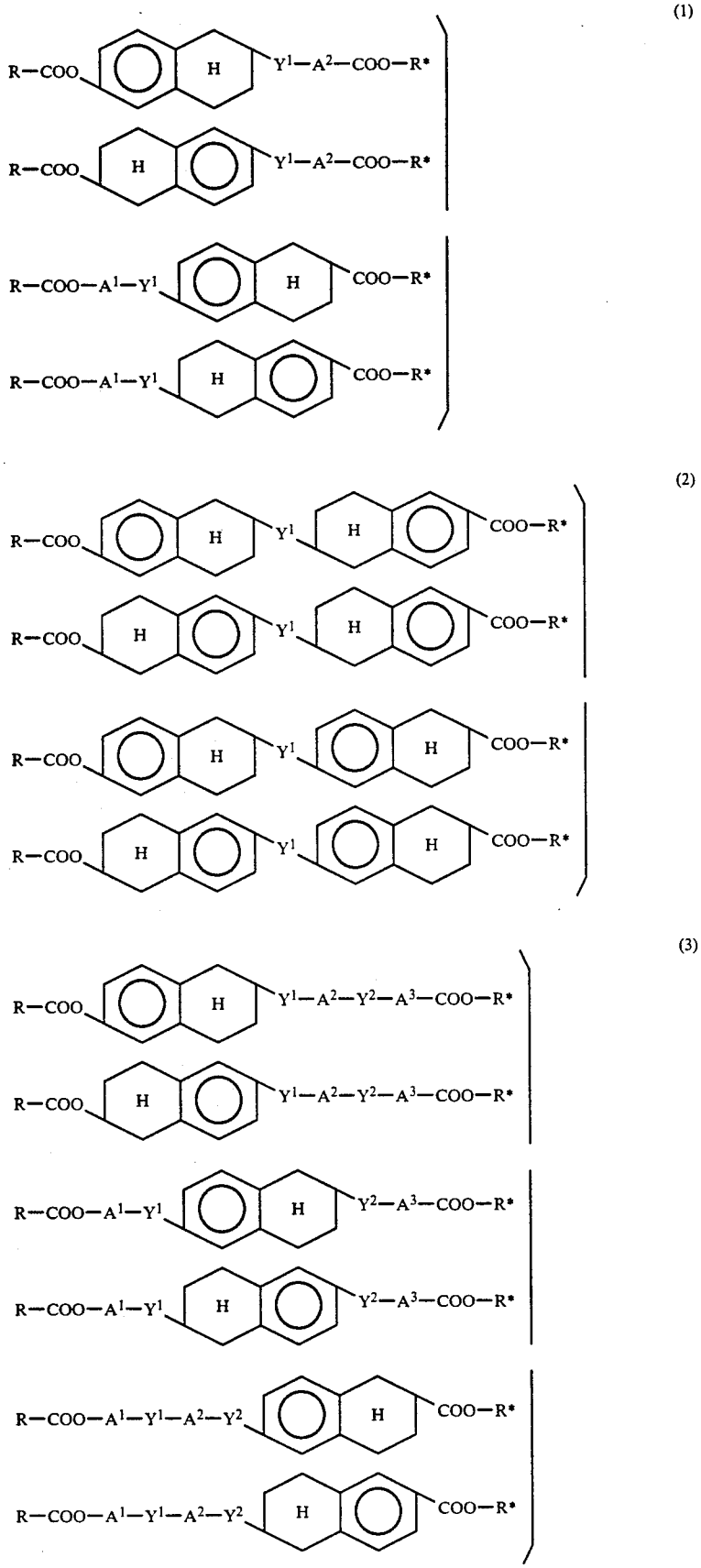

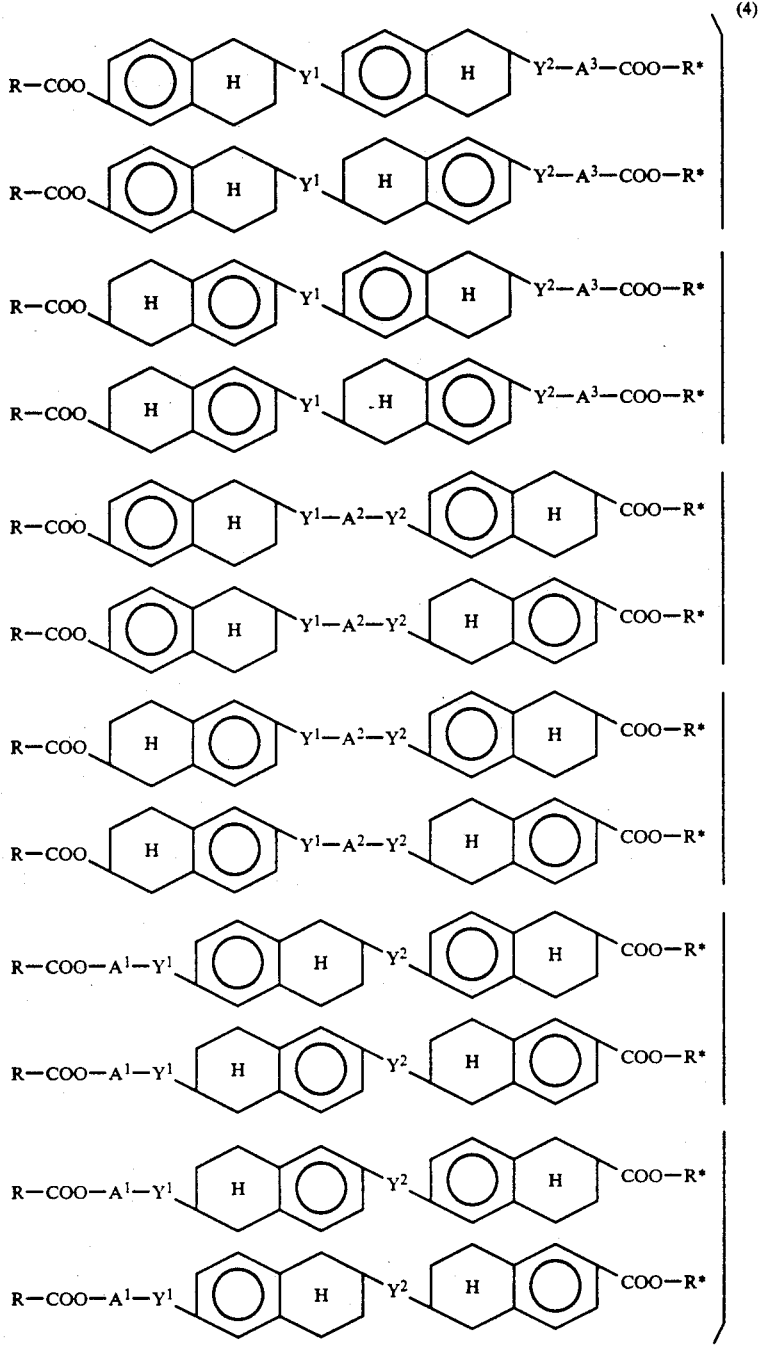

In the above formulas, R* means

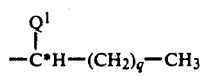

group in the formula [I].

In the above examples, examples in the groups (1) and (2) are those of the carboxylate compound represented by the formula [I] wherein n is 0, and examples in the groups (3) and (4) are those of the carboxylate compound represented by the formula [I] wherein n is 1.

$A^1$, $A^2$ and $A^3$, all of which or a part of which are present in the formula [I] depending upon the above-mentioned condition, are each independently a group selected from the group consisting of the following groups.

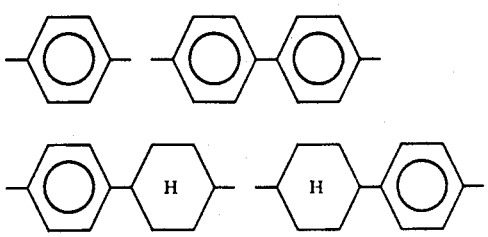

-continued

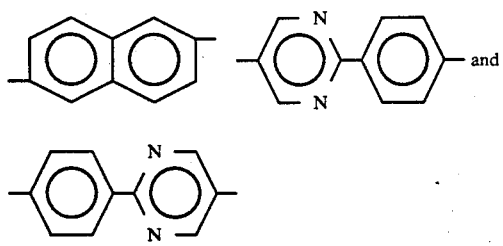

In the above formula [I], $Y^1$ and $Y^2$ are each independently a group selected from the group consisting of —COO—, —CH$_2$CH$_2$— and —CH$_2$O—. When the carboxylate compound of the invention is used as a liquid crystal material, at least one of $Y^1$ and $Y^2$, preferably both of them, are —COO—.

In the above formula [I], $Q^1$ is a group selected from the group consisting of —CH$_3$, —CF$_3$, —C$_2$H$_5$ and —C$_2$F$_5$, and q is an integer of 4 to 12.

Preferred examples of the group R*, namely

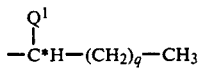

include —C*H(CF$_3$)—C$_6$H$_{13}$, —C*H(CH$_3$)—C$_6$H$_{13}$, —C*H(CH$_3$)—C$_5$H$_{11}$, —C*(C$_2$H$_5$)—C$_5$H$_{11}$ and —C*H(C$_2$H$_5$)—C$_6$H$_{13}$.

Of these groups, preferred is either of the following groups in view of characteristics of the carboxylate compound used as a liquid crystal material into account.

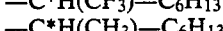
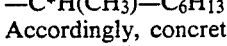

Accordingly, concrete examples of the carboxylate compound represented by the formula [I] are those set forth in Tables 1-1 to 1-2 and Tables 2.

That is, concrete examples of the carboxylate compound represented by the formula [I] wherein n is 0, namely, carboxylate compound represented by the following formula [I-A], are shown in Table 1-1 to Table 1-2.

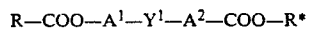  [I-A]

TABLE 1-1

[n = 0]

| Compound Number | R | A$^1$ | Y$^1$ | A$^2$ | R* | Example No. |
|---|---|---|---|---|---|---|
| 1 | C$_7$H$_{15}$— | biphenyl | —COO— | decalin-H | —C*H(CF$_3$)—C$_6$H$_{13}$ | |
| 2 | C$_8$H$_{17}$— | " | " | " | " | |
| 3 | C$_9$H$_{19}$— | " | " | " | " | 1 |
| 4 | C$_{10}$H$_{21}$— | " | " | " | " | |
| 5 | C$_{11}$H$_{23}$— | " | " | " | " | |
| 6 | C$_{12}$H$_{23}$— | " | " | " | " | |
| 7 | C$_{14}$H$_{29}$— | " | " | " | " | |
| 8 | C$_{16}$H$_{33}$— | " | " | " | " | |
| 9 | C$_9$H$_{19}$— | biphenyl | —CH$_2$O— | decalin-H | —C*H(CF$_3$)—C$_6$H$_{13}$ | |
| 10 | " | " | —CH$_2$CH$_2$— | " | " | |
| 11 | C$_9$H$_{19}$— | biphenyl | —COO— | decalin-H | —C*H(CH$_3$)—C$_6$H$_{13}$ | |
| 12 | " | " | " | " | —C*H(CH$_3$)—C$_5$H$_{11}$ | |
| 13 | " | " | " | " | —C*H(C$_2$H$_5$)—C$_5$H$_{11}$ | |
| 14 | " | " | " | " | —C*H(C$_2$H$_5$)—C$_6$H$_{11}$ | |
| 15 | C$_9$H$_{19}$— | phenyl-cyclohexyl-H | —COO— | decalin-H | —C*H(CF$_3$)—C$_6$H$_{13}$ | |
| 16 | C$_9$H$_{19}$— | cyclohexyl-H-phenyl | —COO— | decalin-H | —C*H(CF$_3$)—C$_6$H$_{13}$ | |
| 17 | C$_9$H$_{19}$— | pyrimidinyl-phenyl | —COO— | decalin-H | —C*H(CF$_3$)—C$_6$H$_{13}$ | |

TABLE 1-1-continued
| [n = 0] Compound Number | R | A¹ | Y¹ | A² | R* | Example No. |
|---|---|---|---|---|---|---|
| 18 | $C_9H_{19}-$ | 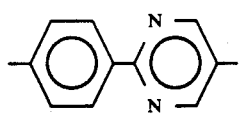 | —COO— | 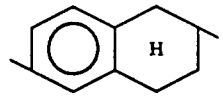 | $-C^*H(CF_3)-C_6H_{13}$ | |
| 19 | $C_9H_{19}-$ | 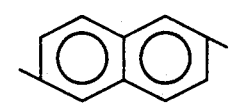 | —COO— | 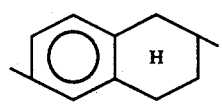 | $-C^*H(CF_3)-C_6H_{13}$ | |
| 20 | $C_9H_{19}-$ | 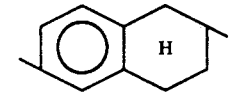 | —COO— | 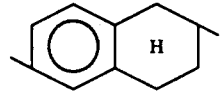 | " | |
| 21 | $C_9H_{19}-$ | 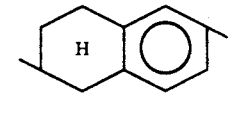 | —COO— | 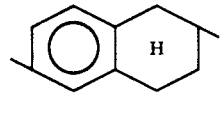 | " | |
| 22 | $C_9H_{19}-$ |  | —COO— | 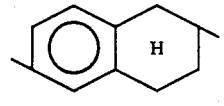 | " | |
| 23 | $C_9H_{19}-$ | 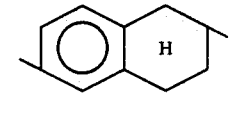 | —COO— | 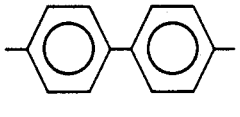 | " | |
| 24 | $C_9H_{19}-$ | 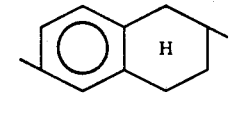 | —COO— | 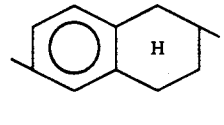 | " | |
| 25 | $C_9H_{19}-$ | 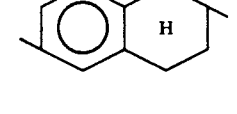 | —COO— | 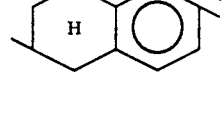 | $-C^*H(CF_3)-C_6H_{13}$ | |
| 26 | $C_9H_{19}-$ | 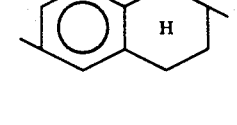 | —COO— | 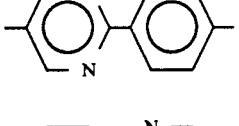 | " | |
| 27 | $C_9H_{19}-$ | 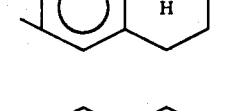 | —COO— | 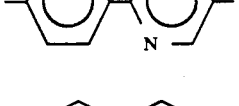 | $-C^*H(CH_3)-C_6H_{13}$ | |
| 28 | $C_9H_{19}-$ | 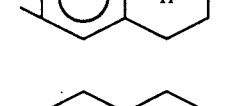 | —COO— | 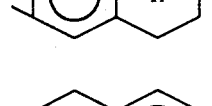 | $-C^*H(CH_3)-C_5H_{11}$ | |
| 29 | $C_9H_{19}-$ | 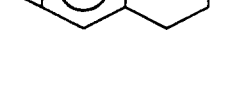 | —COO— | 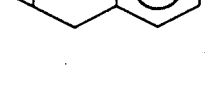 | $-C^*H(C_2H_5)-C_5H_{11}$ | |

TABLE 1-1-continued

[n = 0]

| Compound Number | R | A¹ | Y¹ | A² | R* | Example No. |
|---|---|---|---|---|---|---|
| 30 | $C_9H_{19}-$ | 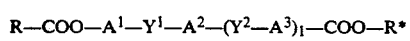 | —COO— | 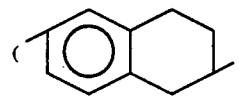 | —C*H($C_2H_5$)—$C_6H_{11}$ | |

Further, concrete examples of the carboxylate compound represented by the formula [I] wherein n is 1, namely, carboxylate compound represented by the following formula [I-B], are shown in Table 2.

R—COO—A¹—Y¹—A²—(Y²—A³)₁—COO—R*  [I-B]

TABLE 2

| Compound No. | R | A¹ | Y¹ | A² | Y² | A³ | R* | Example No. |
|---|---|---|---|---|---|---|---|---|
| 31 | $C_9H_{19}-$ | ![naphthalene-H] | —COO— | ![phenyl] | —COO— | ![phenyl] | —C*H($CF_3$)—$C_6H_{13}$ | 2 |
| 32 | $C_9H_{19}-$ | ![phenyl] | —COO— | ![naphthalene-H] | —COO— | ![phenyl] | —C*H($CF_3$)—$C_6H_{13}$ | |
| 33 | $C_9H_{19}-$ | ![phenyl] | —COO— | ![phenyl] | —COO— | ![naphthalene-H] | —C*H($CF_3$)—$C_6H_{13}$ | |
| 34 | $C_9H_{19}-$ | ![naphthalene-H] | —COO— | ![phenyl] | —COO— | ![phenyl] | —C*H($CF_3$)—$C_6H_{13}$ | |

As shown in Table 3, when used as a liquid crystal material for a liquid crystal element, the above-mentioned carboxylate compound of the invention can be made higher in the switching speed because the alkyl group indicated by R in the formula [I] is bonded to the group A¹ or

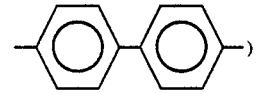

by way of —COO— group, as compared with a compound in which R is directly bonded to the group A¹ or a compound in which R is bonded to the group A¹ by way of —O— group.

TABLE 3

| Compound No. | Compound | Switching time |
|---|---|---|
| 1 | R—CO—O—[naphthalene]—COO—[phenyl]—COO—[phenyl]—COOR* | 80 μsec |
| 2 | R—[naphthalene]—COO—[phenyl]—COO—[phenyl]—COOR* | 1,100 μsec |
| 3 | RO—[naphthalene]—COO—[phenyl]—COO—[phenyl]—COOR* | 2,600 μsec |
| 4 | R—C(=O)—O—[phenyl]—[phenyl]—COO—[cyclohexyl/naphthalene]—COOR* | 120 μsec |

TABLE 3-continued

| Compound No. | Compound | Switching time |
|---|---|---|
| 5 | R—⬡—⬡—COO—[tetralin]—COOR* | 90 μsec |
| 6 | R—O—⬡—⬡—COO—[tetralin]—COOR* | 290 μsec |

Note:
R* means the formula:
$$-\overset{CF_3}{\underset{|}{C^*H}}-C_6H_{13}$$

As is apparent from Table 3, the carboxylate compound indicated by numeral 1 is higher in the switching speed than the compounds indicated by numerals 2 and 3. With respect to the compounds 4–6, the compound indicated by numeral 4 is higher in the switching speed than the compound indicated by numeral 6, and the compound indicated by numeral 4 and the compound indicated by numeral 5 are reversed in the order of the switching speed, but a difference between those compounds in the switching speed is so small that no substantial difference is observed.

The switching time in Table 3 is measured in accordance with a manner described below, and means herein a period of time required for switching from the antiferroelectric state to the ferroelectric state.

MEASUREMENT OF SWITCHING TIME

Figures 9A, 9B:
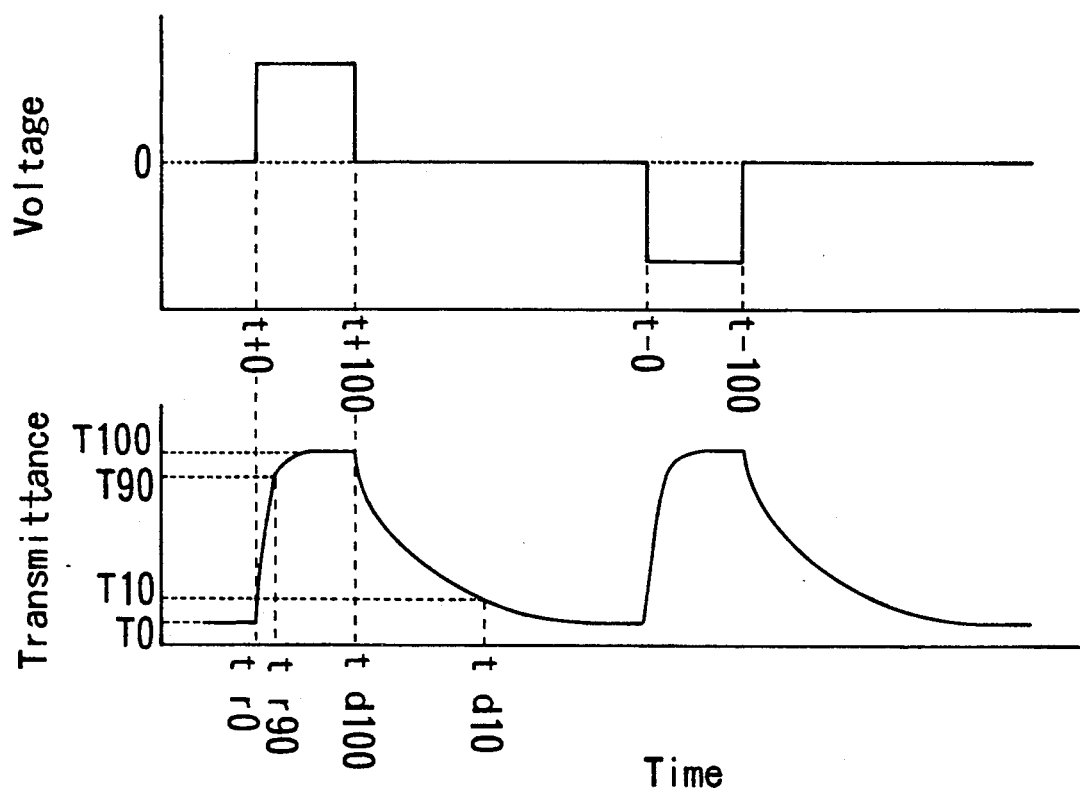
FIGS. 9 (a) and 9 (b) are views of a pulse wave illustrating a method of measuring a switching speed in the invention.

Switching from the antiferroelectric state to the ferroelectric state is referred to as "switching from the AF-state to the F-state", and switching from the ferroelectric state to the antiferroelectric state is referred to as "switching from the F-state to the AF-state". A pulse wave shown in FIGS. 9 (a) and 9 (b) is applied to a test cell, and a transmission coefficient at that time is monitored to obtain a chart Utilizing the chart, the switching time from the AF-state to the F-state and the switching time from the F-state to the AF-state can be calculated by the following formulas. The above-mentioned switching time is measured under the conditions of an electric voltage of 30 V/2 μm, a pulse width of 10 msec and a pulse interval of 90 msec.

Switching time from the AF-state to the F-state $=t_{r_{90}} - t_{r_0}$

Switching time from the F-state to the AF-state $=t_{d_{100}} - t_{r_{10}}$

Further, as shown in Table 4, the carboxylate compound of the invention more easily exhibits a liquid crystal phase in the vicinity of room temperature because the compound has a tetralin ring, as compared with carboxylate compounds having no tetralin ring.

TABLE 4

| No. | Compound | Antiferroelectric phase temperature range |
|---|---|---|
| 1 | R—COO—[tetralin]—COO—⬡—COO—⬡—COOR* | 33–75° C. |
| 2 | R—COO—[naphthalene]—COO—⬡—COO—⬡—COOR* | 66–130° C. |
| 3 | R—COO—⬡—⬡—COO—[tetralin]—COOR* | 43–81° C. |
| 4 | R—COO—⬡—⬡—COO—[naphthalene]—COOR* | — |

Note:
R* has the same meaning as that in Table 3.

As is apparent from Table 4, since the carboxylate compound of the invention indicated by numeral 1 has a tetralin ring, this compound is lower in the temperature range of the antiferroelectric phase than other carboxylate compound having no tetralin ring which is indicated by numeral 2, and the temperature range of the antiferroelectric phase of the compound is in the vicinity of room temperature. Hence, the carboxylate compound of the invention is very useful as a liquid crystal material.

The carboxylate compound as described above can be prepared by means of a combination of known synthesis techniques.

For example, the above-mentioned carboxylate compound can be synthesized in accordance with the following synthesis route.

For example, a mixture of 6-alkoxynaphthalene-2-carboxylic acid and 1,2-diethoxyethane is refluxed while dropwise adding isoamyl alcohol to the mixture in the presence of metallic sodium, to obtain 1,2,3,4-tetrahydro-6-alkoxynaphthalene-2-carboxylic acid.

The 1,2,3,4-tetrahydro-6-alkoxynaphthalene-2-carboxylic acid thus obtained is reacted with acetic acid and hydrobromic acid, to obtain 1,2,3,4-tetrahydro-6-hydroxynaphthalene-2-carboxylic acid.

The 1,2,3,4-tetrahydro-6-hydroxynaphthalene-2-carboxylic acid thus obtained is reacted with benzyl bromide in the presence of potassium hydroxide, to obtain

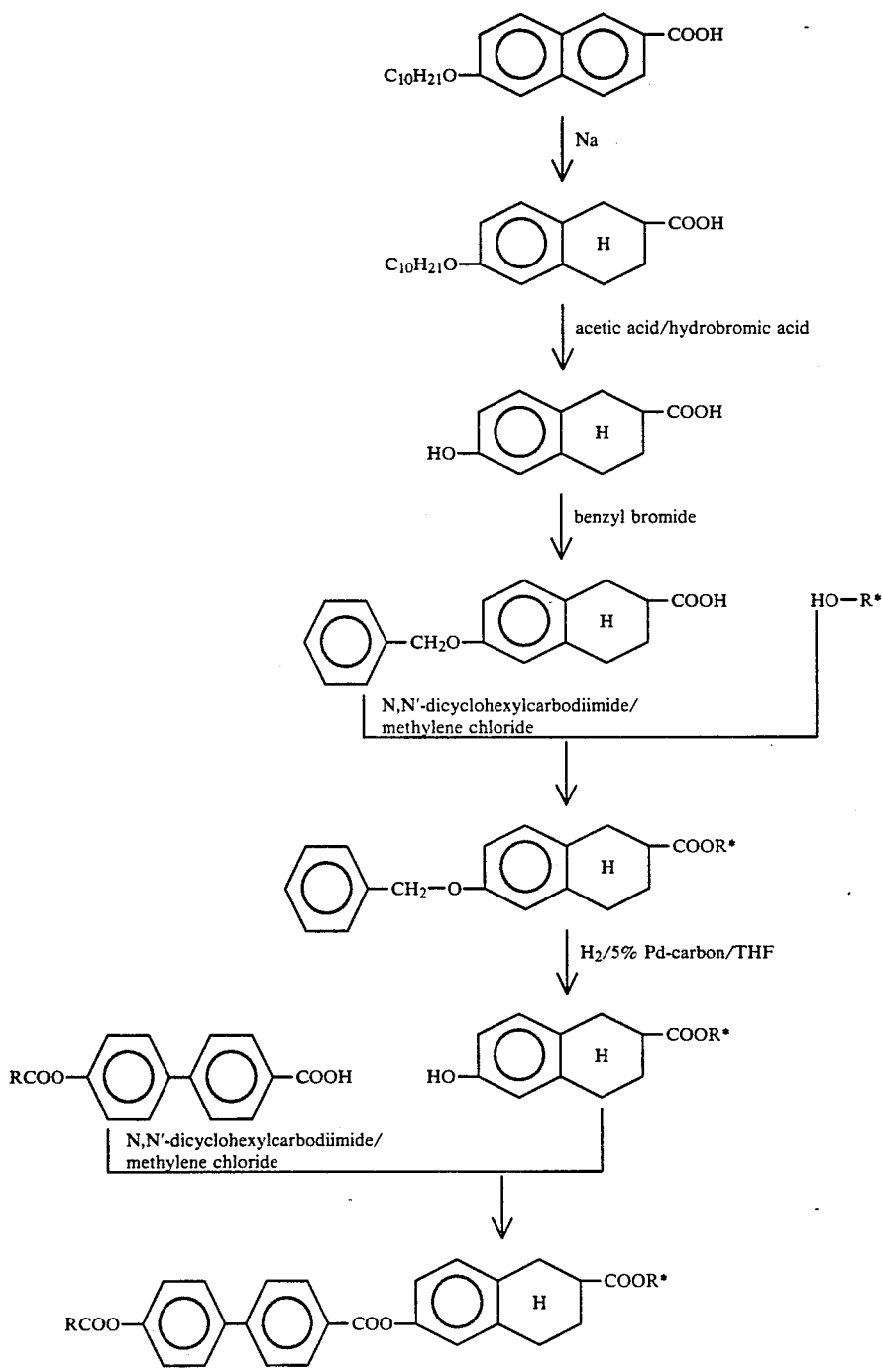

1,2,3,4-tetrahydro-6-benzyloxynaphthalene-2-carboxylic acid.

Subsequently, an alcohol having an asymmetric carbon is reacted with the 1,2,3,4-tetrahydro-6-benzyloxynaphthalene-2-carboxylic acid obtained in the above step in the presence of 4-N,N-dimethylaminopyridine and methylene chloride (as a solvent) while dropwise adding a solution of N,N'-dicyclohexylcarbodiimide, to obtain 1,2,3,4-tetrahydro-6-benzyloxynaphthalene-2-carboxylate.

The 1,2,3,4-tetrahydro-6-benzyloxynaphthalene-2-carboxylate thus obtained is introduced into a solvent such as tetrahydrofuran, and the resulting solution is reduced with hydrogen in the presence of a reducing catalyst such as palladium/carbon to obtain 1,2,3,4-tetrahydro-6-hydroxynaphthalene-2-carboxylate.

Then, 4-alkylcarbonyloxybenzoic acid separately prepared by a conventional process is reacted with the 1,2,3,4-tetrahydro-6-hydroxynaphthalene-2-carboxylate obtained in the above step in the presence of 4-N,N -dimethylaminopyridine and methylene chloride (as a solvent) while dropwise adding a solution of N,N'-dicyclohexylcarbodiimide, to obtain the carboxylate compound of the invention.

The above-described process is one example of a process for preparing the carboxylate compound of the invention, and the carboxylate compound of the invention is in no way limited thereto.

formula, which is one example of the carboxylate compound of the invention, is shown in FIG. 1.

In the following formula, symbols "eq" and "ax" mean equatorial conformation and axial conformation, respectively.

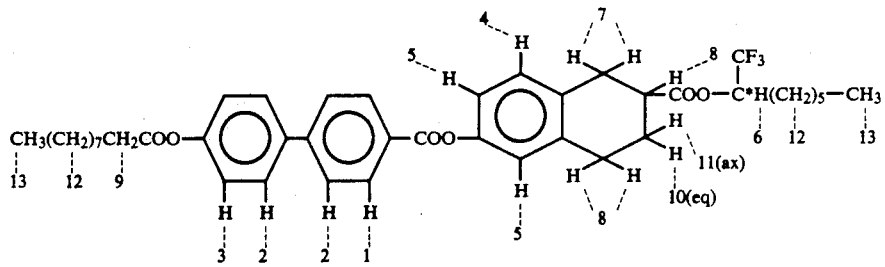

In the above formula, each of numbers 1 to 13 is hydrogen, and these numbers correspond to numbers attached to peaks in FIG. 1.

Figure 2:
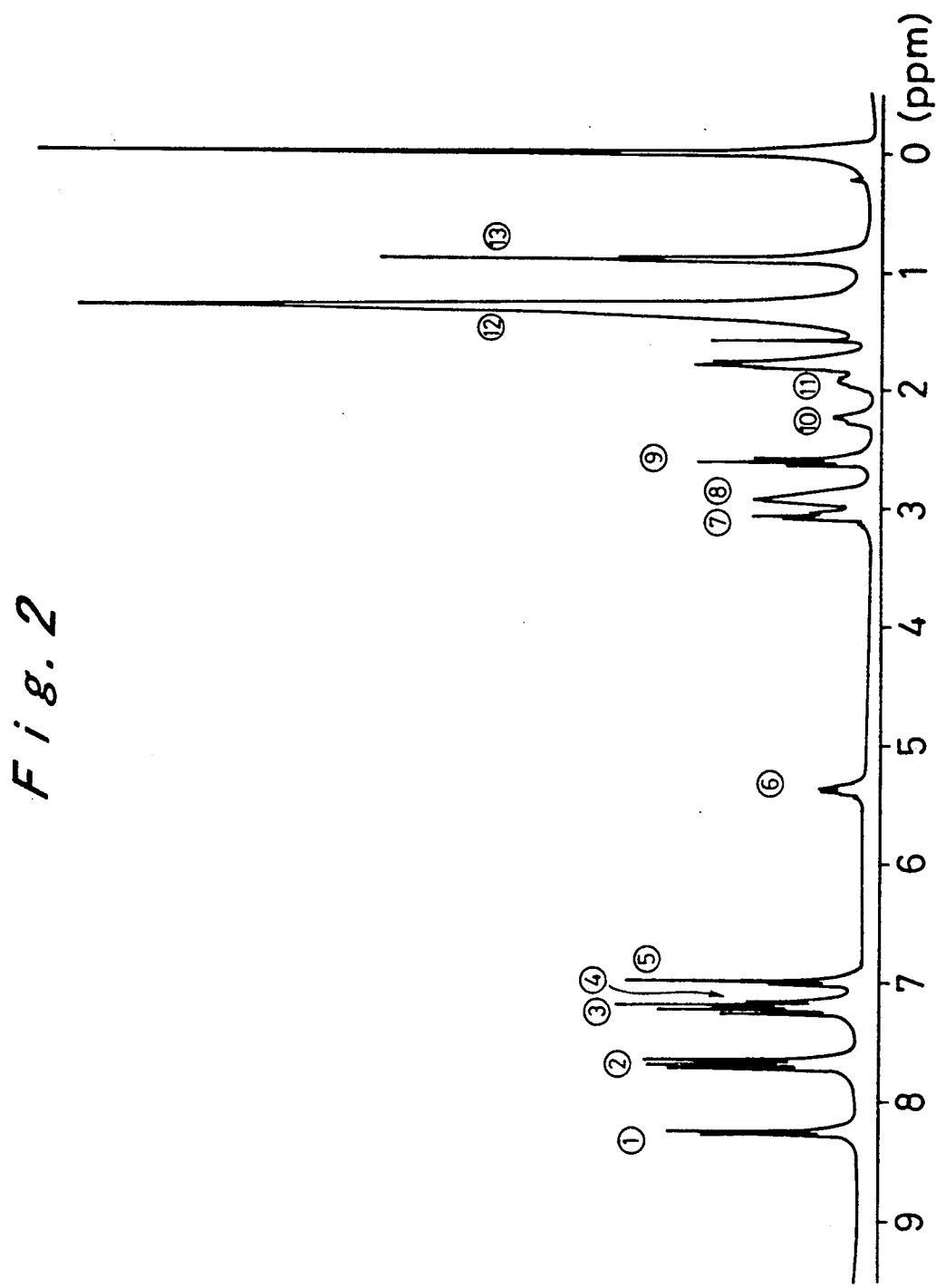
FIG. 2 shows a $^1$H-NMR spectrum of 4-[4'-(6''-decanoyloxy-1'',2'',3'',4''-tetrahydro-2'' -naphthoyloxy)benzoyloxy]benzoic acid R-1'''-trifluoromethylheptyl ester [Exemplified Compound (31)].

A $^1$H-NMR spectrum of 4-[4'-(6''-decanoyloxy-1'',2'',3'',4''-tetrahydro-2''-naphthoyloxy)benzoyloxy]-benzoic acid R-1'''-trifluoromethylheptyl ester [Exemplified Compound (31)] represented by the following formula, which is also one example of the carboxylate compound of the invention, is shown in FIG. 2.

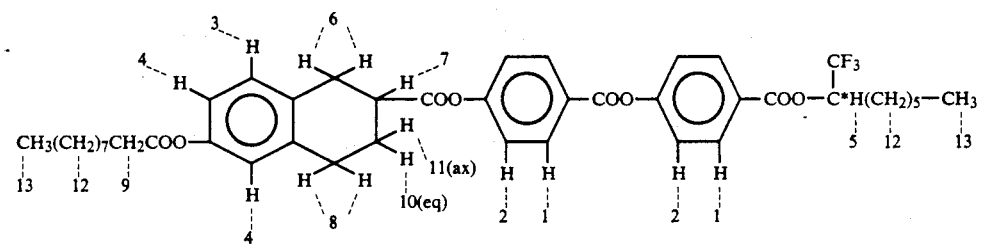

In the above formula, each of numbers 1 to 13 is hydrogen, and these numbers correspond to numbers attached to peaks in FIG. 2.

The carboxylate compound represented by the formula [I] may be used, for example, as a liquid crystal material.

In particular, the carboxylate compound having optical activity may be used as a ferroelectric liquid crystal compound or an antiferroelectric liquid crystal compound.

Of various carboxylate compounds represented by the formula [I], compounds represented by the following formulas [3] and [31] exhibit particularly excellent liquid crystal characteristics.

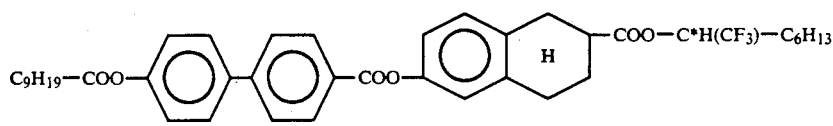

[3]

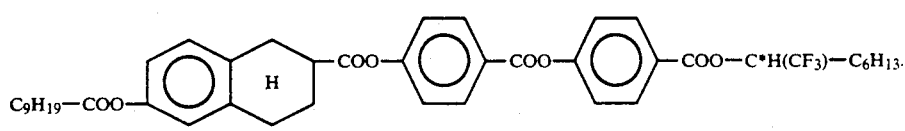

[31]

A $^1$H-NMR spectrum of 6-(4'-decanoyloxybiphenyl-4''-carbonyloxy)-1,2,3,4-tetrahydronaphthalene-2-carboxylic acid R-1'''-trifluoromethylheptyl ester [Exemplified Compound (3)] represented by the following Phase transition temperatures of the compounds represented by the formulas [3] and [31] which are particularly excellent as liquid crystal compounds are shown in Table 5, wherein Cry represents a crystal phase, SmC$_A$* represents an antiferroelectric phase, SmA represents a smectic A phase, and Iso represents an isotropic liquid.

TABLE 5

|  | Cry-SmC$_A$* | SmC$_A$*-SmA | SmA-Iso |
| --- | --- | --- | --- |
| Compound [3] | 33° C. | 75° C. | 103° C. |
| Compound [31] | 33° C. | 81° C. | 135° C. |

In the liquid crystal compounds of the invention, there are many compounds exhibiting a smectic phase over a broad temperature range, as shown in Table 5.

There have been known few liquid crystal compounds which, if used alone as a liquid crystal material, exhibit a smectic phase over such a broad temperature range as in the above-mentioned compounds.

In addition to the fact that the liquid crystal material of the invention exhibits a smectic phase in a broad temperature range, a liquid crystal element comprising such liquid crystal material, for example, an optical switching element, is excellent in response speed.

The liquid crystal material of the invention may be used either singly or in a mixture with other liquid crystal material in the form of a liquid crystal composition. For example, the liquid crystal material of the invention may be used as a major component of a ferroelectric or antiferroelectric liquid crystal composition or as a minor component of a liquid crystal composition which exhibits a smectic phase That is, of the carboxylate compounds of the invention, a carboxylate compound exhibiting a smectic phase can be used as a major component of a liquid crystal composition or as a minor component of a liquid crystal composition which contains other liquid crystal material as a major component, while a carboxylate compound which does not exhibit a smectic phase can be used as an assistant of a liquid crystal composition.

The liquid crystal composition of the invention comprises the carboxylic acid ester compound of the formula [I] and a liquid crystal compound other than the carboxylic acid ester compound Examples of liquid crystal compounds which may be used in combination with the compound of the invention represented by the formula [I] include those listed below.

(+)-4'-(2''-methylbutyloxy)phenyl-6-octyloxynaphthalene-2-carboxylate,

4'-decyloxyphenyl-6-((+)-2''-methylbutyloxy)naphthalene-2-carboxylate,

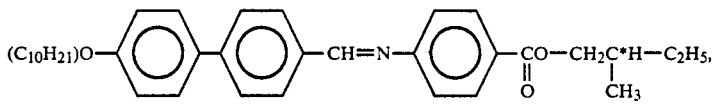

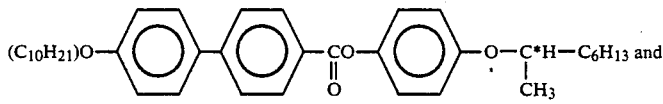

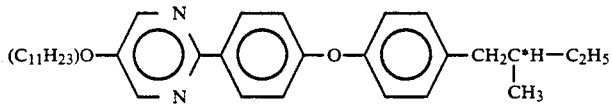

In addition to the above, there may be mentioned the following compounds having a cyclic structure and an optical activity.

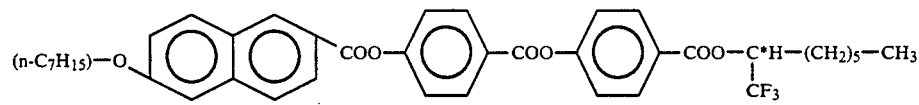

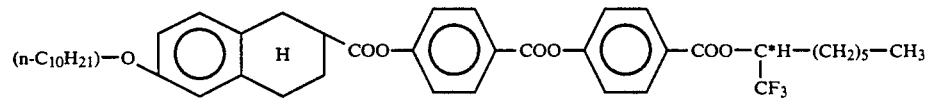

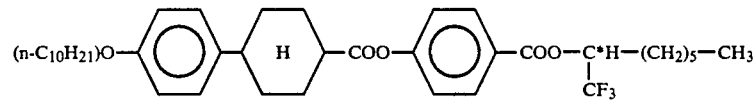

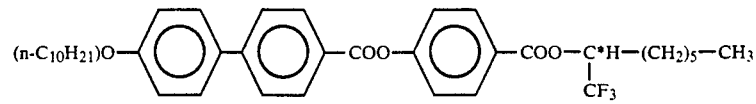

or

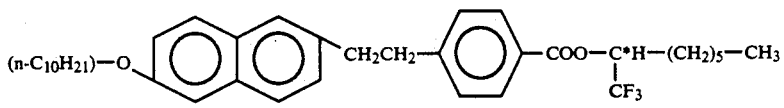
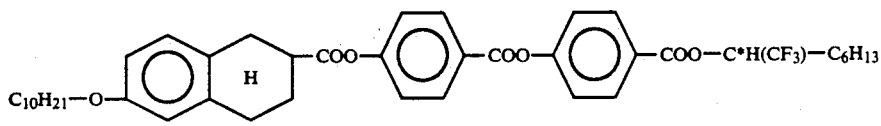
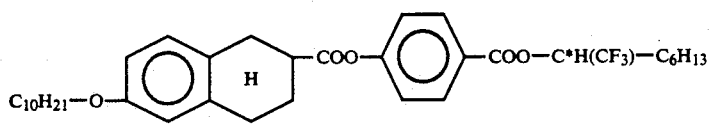
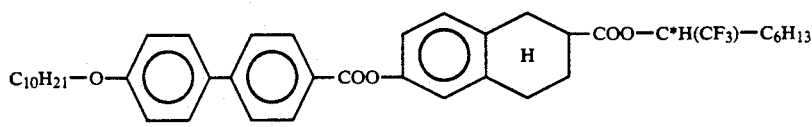

Further, there also may be mentioned Schiff base type liquid crystal compounds such as

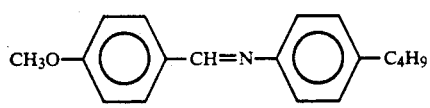

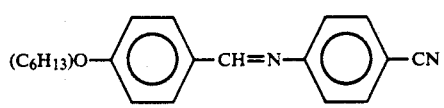

azoxy type liquid crystal compounds such as

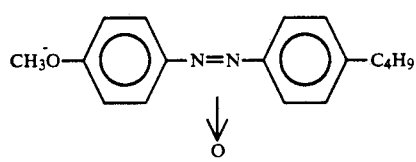

benzoate type liquid crystal compounds such as

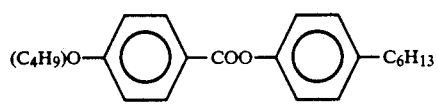

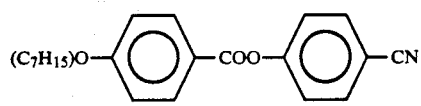

cyclohexylcarboxylate type liquid crystal compounds such as

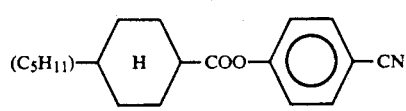

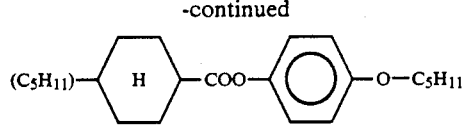

phenyl type liquid crystal compounds such as

terphenol type liquid crystal compounds such as

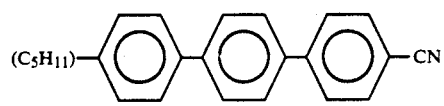

cyclohexyl type liquid crystal compounds such as

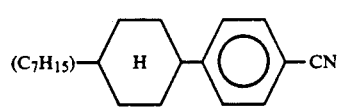

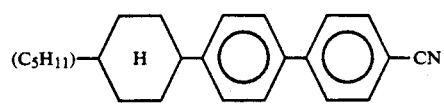

and pyrimidine type liquid crystal compound such as

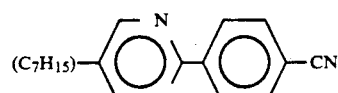

The amount of the carboxylate compound of the formula [I] in the liquid crystal composition can be optionally determined in consideration of characteristics of the resulting composition. The composition of the invention contains the carboxylate compound of the formula [I] in an amount of usually 1-99 parts by weight, preferably 5-75 parts by weight, based on 100 parts by weight of the total amount of liquid crystal materials contained in the composition.

In addition to the liquid crystal materials mentioned above, the liquid crystal composition may further contain additives conventionally used in liquid crystal compositions, for example, conductivity-imparting agents and life-improving agents.

The liquid crystal composition of the invention can be prepared by mixing the above-mentioned carboxylate compound with other liquid crystal material, and if desired, additives.

When a voltage is applied to the liquid crystal composition (liquid crystal material) comprising the aforementioned liquid crystal material, an optical switching phenomenon takes place. Utilizing this phenomenon, a display device exhibiting a high response can be produced In the invention, with regard to elements utilizing such phenomenon or methods of driving such elements, reference to for example Japanese Patent L-O-P Publns. Nos. 107216/1981 and 118744/1984 may be made.

The liquid crystal material that may be used in the display device referred to above may include such compounds as exhibiting any of smectic C phase, smectic F phase, smectic G phase, smectic H phase, smectic I phase, smectic J phase and smectic K phase Display devices using liquid crystal material exhibiting other phases than the smectic C phase generally have a low response speed, and hence it has heretofore been considered that it is effective to drive a display device by means of a liquid crystal material exhibiting the smectic C phase having a high speed response.

However, it has been found that it is possible in the invention to advantageously use the liquid crystal material even when it exhibits a smectic A phase other than the smectic C phase by utilizing a method where the display device is driven by means of a liquid crystal material exhibiting a smectic A phase as proposed by the present inventors in Japanese Patent L-O-P Publn. Nos. 3632/1989 and 918/1990. That is, by virtue of utilization of this driving method, the liquid crystal element of the invention can be driven in a wide phase range, and at the same time, it is possible to speed up an electro-optical response.

Figure 3:
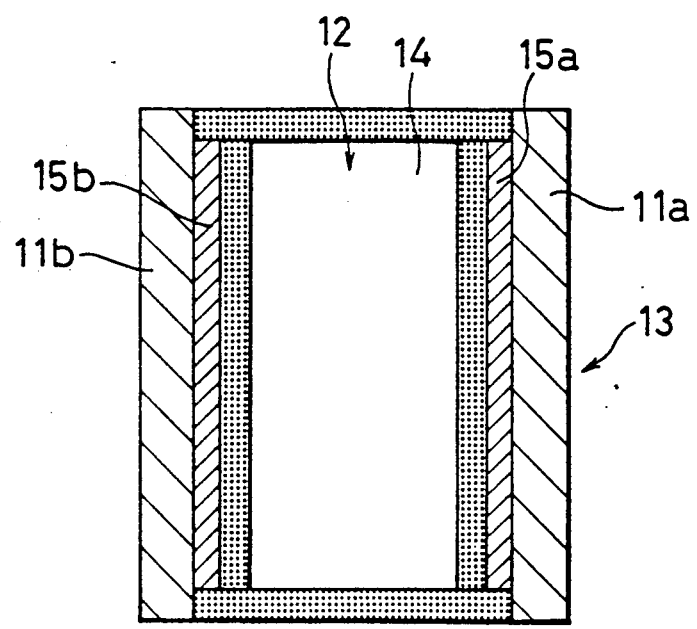
FIG. 3 is a schematic sectional view of a liquid crystal element of the present invention.

The liquid crystal element of the invention is composed of a cell filled with a liquid crystal material or composition, and polarizing plates. In detail, the liquid crystal element of the invention, for example, as shown in FIG. 3, is formed from a cell 13 comprising two transparent substrates 11a and 11b arranged so as to form a gap 14 to be filled with a liquid crystal material 12, and transparent electrodes 15a and 15b formed on the surfaces of the transparent substrates 11a and 11b, said surfaces individually facing the liquid crystal material 12, the liquid crystal material 12 charged in the gap 14 of the cell 13, and polarizing plates (not shown) arranged outside at both sides of the cell 13.

In the invention, employable as the substrate are, for example, glass and transparent polymer plates. When glass substrates are used, the substrate surfaces may be provided with an undercoat layer (i.e., layer for inhibiting permeation of unnecessary component) comprising silicone oxide as a major component to prevent deterioration of the liquid crystal material caused by elution of alkali component of the glass. The transparent substrate, for example, glass substrate, usually have a thickness of 0.01-1.0 mm.

In the invention, flexible transparent substrates may be used as the transparent substrates. In this case, one of the substrates may be a flexible transparent substrate, or both substrates may be flexible transparent substrates. Useful as such flexible transparent substrates are polymer films. When the flexible transparent substrates are used as the transparent substrates, it is preferred that a thickness t (mm) of each flexible transparent substrate, a modulus of elasticity E (kgf/m²) and a width a (mm) of the gap formed in the cell have the following relationship.

$$\frac{a^4}{Et^3} < 0.32$$

Each of the transparent substrates as mentioned above is provided with a transparent electrode on the surface. The transparent electrode is formed, for example, by coating the transparent substrate surface with iridium oxide, tin oxide, etc. The transparent electrode can be prepared by a known method. The thickness of the transparent electrode is usually in the range of 100 to 2,000 Å.

The transparent substrate having the transparent electrode may be further provided with an orientation layer or a ferroelectric material layer on the surface of the transparent electrode. The orientation layer includes, for example, an organic thin film formed by chemical adsorption thereon of an organic silane coupling agent or a carboxylic acid polynuclear complex, and an inorganic thin film. Examples of the organic thin film include thin films of polymers such as polyethylene, polypropylene, polyester, polyamide, polyvinyl alcohol and polyimide. The organic thin films may be formed by such techniques as coating, adhesion, deposition or polymerization (e.g., plasma polymerization) on the substrate.

Examples of the inorganic thin film include thin films of oxides such as silicon oxide, germanium oxide and alumina, thin films of nitrides such as silicon nitride, and thin films of other semi-conductors. The inorganic thin films may be formed by such techniques as deposition (e.g. rhombic deposition) and sputtering.

The thin film as mentioned above is imparted with orientation by imparting anisotropism or stereospecificity to the thin film itself in the film forming procedure, or externally imparting orientation to the thin film after the film formation procedure. Specifically, there may be mentioned a method in which the thin film is formed by coating a polymer such as polyimide resin on the transparent electrode, followed by rubbing the film in a definite direction; a method in which a polymer film is subjected to stretching to impart orientation to the stretched film; and a method in which an oxide is subjected to rhombic deposition to form the oriented oxide film.

Such thin film (for example, orientation layer) may be so formed that it also serves as a spacer described later.

Two transparent substrates as mentioned above are arranged so that the transparent electrodes formed on the substrates face each other and a gap to be filled with a liquid crystal material or composition is formed by these two transparent substrates. The gap thus formed has a width of usually 1-10 μm, preferably 1-5 μm.

Such gap may be formed, for example, by arranging two substrates so as to hold a spacer between them. Usable as the spacer is a polyimide polymer obtained, for example, by patterning a photosensitive polyimide precursor. By the use of the spacer, a monodomain is formed by the interfacial effect between the spacer and the liquid crystal material.

Figure 4A:
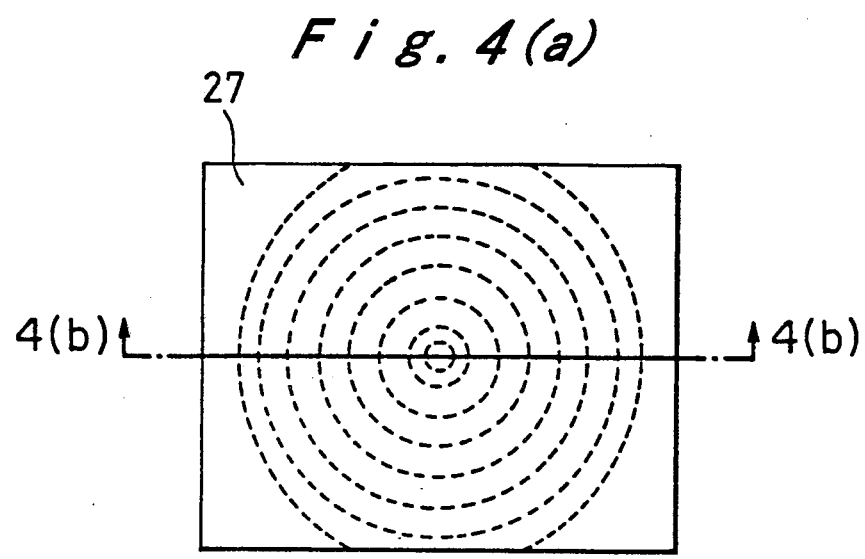
FIG. 4 (a) shows a liquid crystal element having a concentric spacer, and FIG. 4 (b) is a sectional view taken on line 4 (b)—4 (b) of FIG. 4 (a).
Figure 4B:
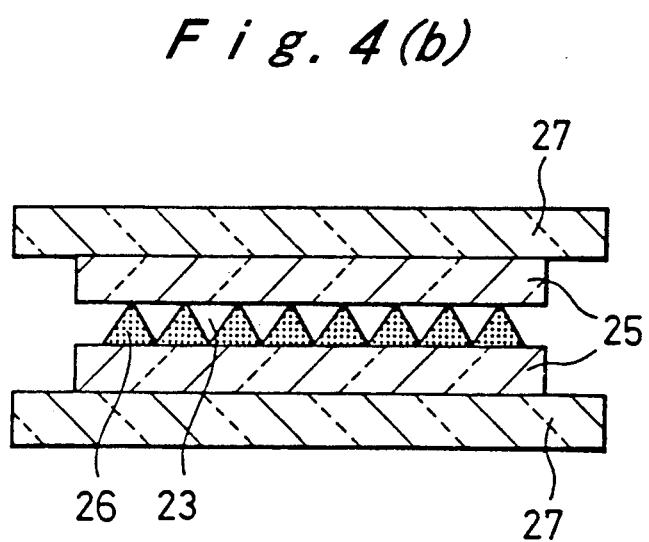

As shown in FIG. 4 (a) and, FIG. 4 (b) that is a sectional view taken on line 4 (b)—4 (b) of FIG. 4 (a), integration of the orientation film with the spacer may be made, for example, by using a concentric spacer 26 which acts as an orientation film. In FIG. 4 (a) and FIG. 4 (b), the transparent substrates are indicated by numeral 27, the transparent electrodes are indicated by numeral 25, and the liquid crystal material is indicated by numeral 23.

Figure 5A:
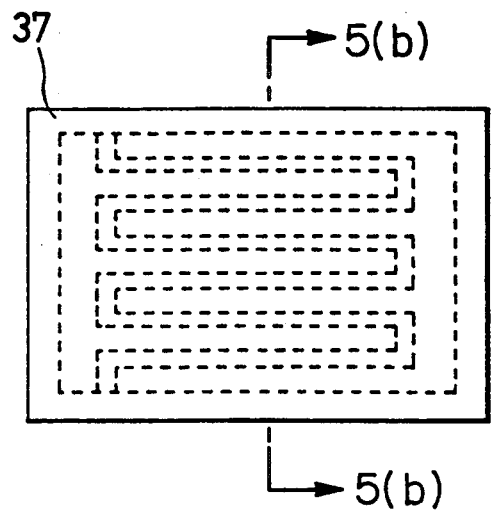
FIG. 5 (a) shows a liquid crystal element having a comb-shaped spacer, and FIG. 5 (b) is a sectional view taken on line 5 (b)—5 (b) of FIG. 5 (a).
Figure 5B:
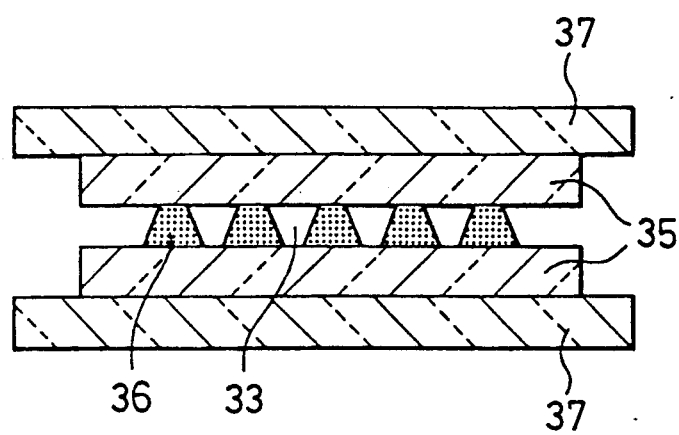

As shown in FIG. 5 (a) and FIG. 5 (b) that is a sectional view taken on line 5 (b)—5 (b) of FIG. 5 (a), integration of the orientation film with spacer may be made, for example, by using a comb-like spacer 36 which acts as an orientation film. In FIG. 5 (a) and FIG. 5 (b), the transparent substrates are indicated by numeral 37, the transparent electrodes are indicated by numeral 35, and the liquid crystal material is indicated by numeral 33.

Figure 6:
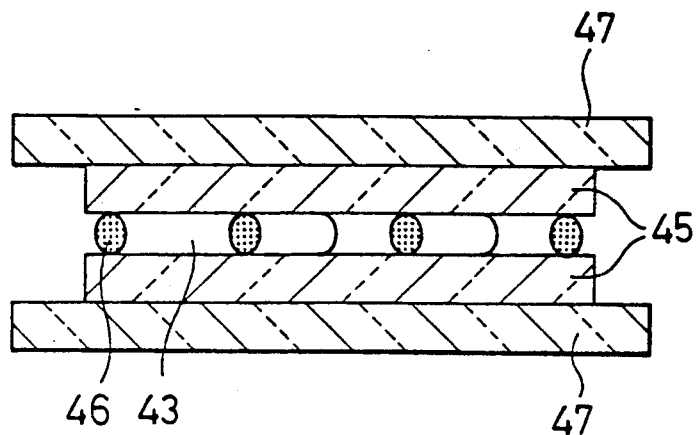
FIG. 6 is a sectional view showing a structure of a liquid crystal element of the present invention which uses a fiber as a spacer.

As shown in FIG. 6, fibers 46 may be incorporated into a liquid crystal material 43 instead of using the above-mentioned spacer. In this case, a definite gap is held between the transparent substrates 47 provided with transparent electrodes 45 owing to the fibers.

The fibers used herein preferably has the following relationship between an average diameter and an average length of the fibers.

$$3 \leq \frac{q}{d} \leq 100$$

wherein d is an average diameter of the fibers, and q is an average length of the fibers.

Various kinds of fibers are employable as the fibers, but preferred are those obtained by spinning alkali glass.

It is also possible to incorporate particulate materials into the liquid crystal material in place of or in combination with the above-mentioned fibers.

The particulate materials include those of melamine resin, urea resin or benzoguanamine resin having a particle diameter of 1–10 μm.

The two transparent substrates arranged so as to form the gap in the manner mentioned above are combined together by sealing their peripheries with a sealer. Useful as the sealer are, for example, epoxy resin and silicone resin. The epoxy resin or the like used as the sealer may be modified with acrylic materials or silicone rubbers.

The gap of the liquid crystal cell having such a structure as mentioned above is filled with a liquid crystal material comprising the carboxylate compound represented by the aforementioned formula [I].

The liquid crystal material filled in the gap of the liquid crystal cell may be oriented, for example, by utilizing a monoaxial orientation control method such as a temperature gradient method using a spacer edge or a surface treatment method using an orientation film. In the invention, it is also possible to carry out initial orientation of the liquid crystal material, for example, by applying a direct bias voltage to the liquid crystal material while heating the material.

Figure 7:
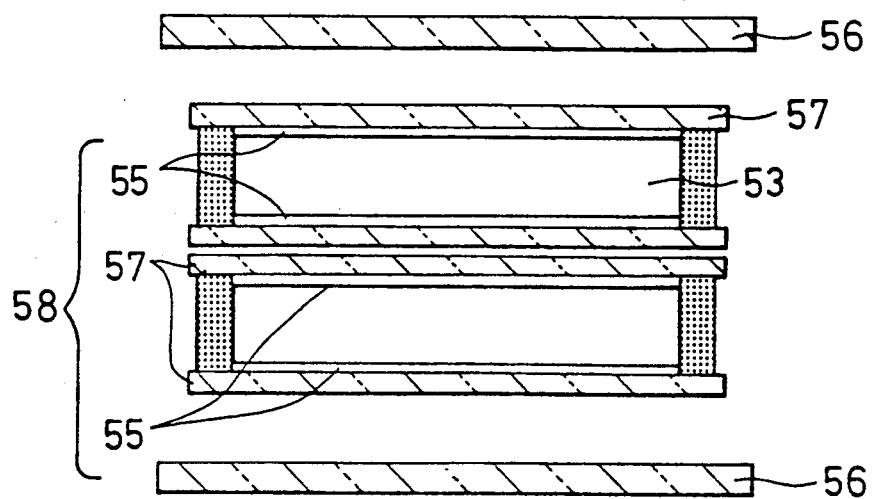
FIG. 7 is a sectional view showing a structure of a liquid crystal element of the invention in which a cell is disposed between two polarizing plates.

The liquid crystal cell filled with the liquid crystal material and subjected to initial orientation as described above is disposed between two polarizing plates. As shown in FIG. 7, two or more cells 58 each of which comprises two transparent substrates 57 and two transparent electrodes 55 and is filled with a liquid crystal material 53 may also be disposed between two polarizing plates 56.

In the liquid crystal element of the invention, two polarizing plates can be disposed so that planes of polarization of the polarizing plates meet at an angle of 70°–110°. Preferably, the polarizing plates are disposed so that the directions of polarized lights of the two polarizing plates meet at right angles, namely, at an angle of 90°.

Usable as the polarizing plates are polarizing films which are imparted with polarizing properties by stretching a resin film such as a polyvinyl alcohol resin film or a polyvinyl butyral resin film in the presence of iodine or the like so as to allow the film to absorb the iodine. The polarizing film may have a multi-layer construction by coating its surface with other resin.

In the present invention, the above-mentioned liquid crystal cell may be disposed between two polarizing plates having been arranged as described above so that a rotation angle of the cell is within the range of ±10° from the state wherein the an amount of transmitted light is the least (i.e., the darkest state), preferably the darkest state is attained. The liquid crystal cell ma also be disposed between the polarizing plates having been arranged as described above so that a rotation angle of the cell is within the range of ±10° from the state wherein an amount of transmitted light is the most, (i.e., the brightest state), preferably the brightest state is attained.

The liquid crystal element of the invention can be prepared, as shown in FIG. 3, by filling the gap 14 of the cell 13 with the liquid crystal material 15 mentioned above and subjecting the crystal material 15 to initial orientation.

The liquid crystal material 15 is heated usually until it reaches a molten state, and the molten material is injected into the vacuumized gap 14 of the cell 13 through an inlet provided in the cell. After the injection operation, the inlet is sealed.

After sealing the inlet, the cell 13 is heated to a temperature higher than the temperature at which the liquid crystal material 15 filled in the cell 13 exhibits an isotropic phase, and then the cell is cooled to a temperature at which the liquid crystal material 15 exhibits a liquid crystal state.

The cooling is carried out at a rate of, preferably not more than 2° C./min, more preferably 0.1°–2.0° C./min, particularly preferably 0.1–0.5° C./min. By cooling the cell 13 at such a cooling rate as mentioned above, the state of initial orientation of the liquid crystal material 15 is improved, and thereby a liquid crystal element having a liquid crystal phase consisting of a monodomain of less orientation defect can be easily prepared. The initial orientation referred to herein implies the state of arrangement of the liquid crystal material prior to changing orientation vector of the liquid crystal material by applying a voltage to the material.

The liquid crystal element of the invention prepared as above is markedly excellent in characteristics such as contrast as compared with conventional liquid crystal elements, and hence the element of the invention can be favorably used as, for example, a surface stabilized ferroelectric liquid crystal element, a helical modulation element, an excess scattering element, a guest-host element and a vertical orientation liquid crystal element.

In the case where the liquid crystal element of the invention is driven by applying thereto an electric field, the electric field is controlled to have a frequency of usually 1 Hz to 100 KHz, preferably 10 Hz to 10 KHz, and to have a voltage of usually 0.01 to 60 Vp-p/$\mu$m$^t$ (voltage per thickness of 1 $\mu$m), preferably 0.05 to 30 Vp-p/$\mu$m$^t$.

When the liquid crystal element of the invention using an optically active liquid crystal material comprising the carboxylate compound represented by the aforementioned formula [I] is driven by application of an electric field, two kinds of hysteresis curves of the transmitted light through the liquid crystal element are drawn, by changing a width of the wave (driving wave) of the electric field to be applied. One of the hysteresis curves is drawn by a driving method in which a so-called bi-stability of the liquid crystal material is utilized, and the other is drawn by a driving method in which a so-called tri-stability of the liquid crystal material is utilized.

The liquid crystal element of the invention in which a liquid crystal cell filled with the optically active liquid crystal material is disposed between two polarizing plates which are arranged so that the polarizing planes cross at right angles and the darkest state is attained when no electric field is applied, may be driven, for example, by application of an electric field of any wave form having a frequency of 50 Hz to 100 KHz, preferably 70 Hz to 10 KHz, such as rectangular wave (or pulse wave), triangular wave, sine wave and a combination thereof. For example, when an electric field of rectangular wave or pulse wave or combination thereof is applied, the driving speed of the liquid crystal element can be increased by setting a width of the electric field to not more than 10 millisec., preferably within a range of 0.01 to 10 millisec. In this range, the liquid crystal element of the invention can be used as a liquid crystal element having a bi-stability. On the other hand, by setting the width of the electric field to more than 10 millisec., preferably within a range of 33 to 1,000 millisec., the liquid crystal element of the invention can be used as a liquid crystal element having a tri-stability in the region where not so high driving speed is required. The term "width of the electric field" used herein means that, in the electric field of rectangular wave, for example, the time span for which a designated voltage is maintained.

By using the liquid crystal element of the invention, various liquid crystal display devices and electro-optical display devices can be manufactured. The liquid crystal element of the invention which is filled with a liquid crystal material exhibiting a smectic phase may be used for manufacturing a memory-type liquid crystal display device or an electro-optical display device incorporated with, for example, a thermal-write or laser-write type liquid display element. Further, in addition to the above-mentioned uses, by the use of a liquid crystal material comprising a carboxylate compound having ferroelectricity, there can be manufactured a liquid crystal display device or an electro-optical display device incorporated with, for example, an optical switching element for an optical shutter or a liquid crystal printer, a piezoelectric element and a pyroelectric element.

That is, the liquid crystal material of the invention exhibits the tri-stability or bi-stability, and hence the liquid crystal element of the invention can be allowed to have optical switching function or display function by inverting the electric field so as to attain the tri-stabile state or bi-stable state.

The liquid crystal material exhibiting the bi-stability has a spontaneous polarization, and hence when a voltage is applied once to the liquid crystal element comprising this liquid crystal material, the liquid crystal element keeps a memory effect even after elimination of the electric field. That is, it is not necessary to apply continuously the electric field to the liquid crystal element in order to keep this memory effect. Accordingly, in the display device using the liquid crystal element of the invention, the consumption of electric power can be reduced. Also in the case the liquid crystal element comprising the liquid crystal material exhibiting the tri-stability, the memory effect can be maintained. Moreover, a display device using such liquid crystal element is very clear because of stable contrast.

Further, in the switching element of the invention comprising the liquid crystal material represented by the aforementioned formula [I], it is possible to perform switching operation only by changing the direction of orientation of the molecule. In this case, the first order of the field strength acts on the driving of the switching element, and hence the switching element of the invention can be driven at a low voltage.

By using this switching element, a high speed response of not longer than several 10 $\mu$ seconds can be attained, and hence the operating time of the element can be shortened sharply. Accordingly, a display (liquid crystal display device) having large numbers of scanning lines and a large screen can be easily manufactured by using the liquid crystal element of the invention. Moreover, this display can be driven without using an auxiliary means for controlling a driving temperature, because it can be driven at room temperature or lower.

Further, when an electric field is applied to the liquid crystal material used in the invention, inclination of the molecule of the material is induced even in a smectic A phase which has been generally considered not to exhibit a bi-stability, and hence optical switching can be performed in this phase by utilizing such properties of the liquid crystal material. That is, it has been considered that when ferroelectric liquid crystal compounds are used, a practical response speed cannot be attained, and the smectic A phase thereof is not used generally. However, it is possible to drive a display device using the liquid crystal element of the invention by utilizing a driving method and an apparatus proposed by the present inventors in Japanese Patent L-O-P Publn. Nos. 3632/1989 and 918/1990. Further, the liquid crystal material used in the invention exhibits two or more stable states even in the smectic F phase which is in better order than the smectic C phase, and hence optical switching can be performed in the same manner as described above by utilizing plural stable states in this phase.

The display device using the liquid crystal element of the invention may be driven by various methods, and concrete examples of those methods are described below.

The first method comprises interposing the liquid crystal element of the invention between two polarizing plates, applying an external voltage to the liquid crystal element to change an orientation vector of the liquid crystal material filled in the element, and thereby per-forming display utilizing birefringence caused by the two polarizing plates and the liquid crystal material.

The second method is to utilize dichroism of a dichromic dye incorporated in a liquid crystal material. This method is to perform display by changing the orientation direction of the liquid crystal compound to cause a change of wavelength of light absorbed by the dye. The dye which may be used in this case generally is a dichromic dye, and examples thereof include azo dyes, naphthoquinone dyes, cyanine dyes and anthraquinone dyes.

The display device prepared by using the liquid crystal element of the invention may be driven by an electric address display system, an optical address display system, a heat address display system and a light beam display system, wherein any of driving means such as static drive, simple matrix drive and composite matrix drive may be employed.

Figure 8A:
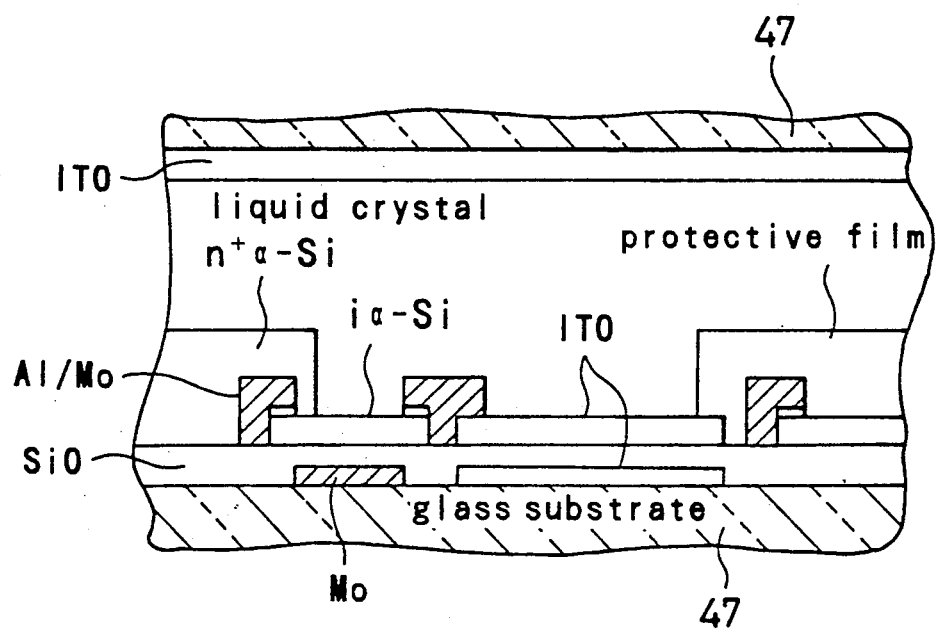
FIG. 8 (a) shows an example of a nonlinear element, and FIG. 8 (b) shows an example of a three-terminal element.
Figure 8B:
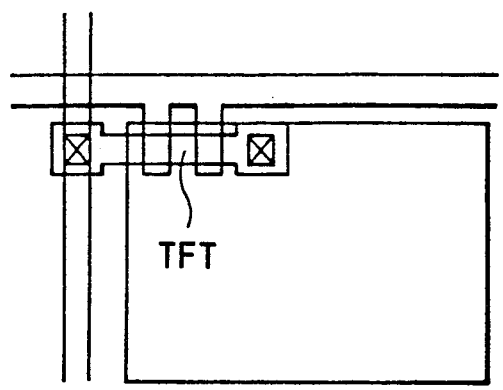

Further, when the display device in the invention is driven by application of an electric field, a nonlinear element or an active element can be used as an element for driving each picture element. More particularly, as a nonlinear element of two-terminal element, there may be mentioned, for example, an element utilizing nonlinearities of a varistor, MIM (Metal Insulator Metal) and diode arranged on one transparent substrate, as shown in FIG. 8 (a). Further, as an active element of three-terminal element, there may be mentioned, for example, an element in which TFT (thin film transistor), Si-MOS (Si-metal oxide semiconductor field-effect transistor) or SOS (Silicon on Sapphire) is arranged on a picture element, as shown in FIG. 8 (b).

EFFECT OF THE INVENTION

As described above, a novel carboxylate compound is provided by the present invention.

The novel carboxylate compound is optically active. Further, in the compound, 1,2,3,4-tetrahydronaphthalene ring and benzene ring are linked by means of an ester linkage, and when two benzene rings exist, these benzene rings are also linked by means of an ester linkage. For these reasons, the carboxylate compound exhibits a smectic phase over a wide temperature range including room temperature, and can be used as a ferroelectric liquid crystal material or an antiferroelectric liquid crystal material.

By combining the liquid crystal material of the invention with the same or different kind of liquid crystal material, the temperature range where the liquid crystal exhibits effective properties can be widened without marring ferroelectricity or antiferroelectricity of the liquid crystal material of the invention.

Accordingly, by the use of such liquid crystal material, a liquid crystal element having a high speed response in a wide temperature range can be obtained.

Further, in a liquid crystal display prepared by using such element, the operating time can be shortened sharply. In addition, the consumption of electric power can be reduced, and a high contrast and a stable contrast can be obtained. Moreover, the liquid crystal display can be driven at a low voltage.

When the carboxylate compound of the invention is used as an antiferroelectric liquid crystal compound, the memory characteristics may be obtained without difficulty, and the orientation characteristics may also be improved.

By the use of the liquid crystal material of the invention, there can be obtained various devices having excellent characteristics such as wide operating temperature range, high (fast) switching speed, very small consumption of electric power, and stable contrast.

The present invention is further described below with reference to examples, but it should be construed that the invention is in no way limited to those examples. In the examples, R and S mean R body and S body of an optically active material, respectively.

EXAMPLE 1

Synthesis of 6-(4'-decanoyloxybiphenyl-4"-carbonyloxy -1,2,3,4-tetrahydronaphthalene-2-carboxylic acid R-1'''-trifluoromethylheptyl ester [Exemplified Compound (3)]

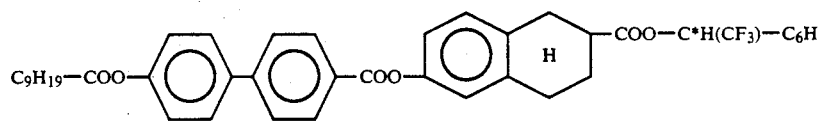

[3]

FIRST STAGE

To a mixture of 3.86 g (11.8 mmol) of 6-decyloxynaphthalene-2-carboxylic acid and 130 ml of 1,2-diethoxyethane was added 3.0 g (130 mg atom) of metallic sodium with stirring at 120° C. in a nitrogen atmosphere, and the resulting mixture was heated to a reflux temperature.

To the mixture was dropwise added 10 g (114 mmol) of isoamyl alcohol over 1 hour, and they were reacted with each other for 11 hours under reflux. After cooling of the reaction system to room temperature, to the reaction mixture was added ethanol to decompose the remaining metallic sodium. Then, the reaction mixture was made acidic using 20% hydrochloric acid.

To the reaction mixture was added 100 ml of water, then the resulting organic phase was separated from the mixture, and the organic phase was washed with water.

The organic phase was concentrated under a reduced pressure to obtain 4.25 g of a solid. This solid was recrystallized with toluene to obtain 2.95 g (8.89 mmol) of 1,2,3,4-tetrahydro-6-decyloxynaphthalene-2-carboxylic acid.

SECOND STAGE

A mixture of 16.6 g (50 mmol) of the 1,2,3,4-tetrahydro-6-decyloxynaphthalene-2-carboxylic acid obtained in the first stage, 250 ml of acetic acid and 86.5 g (0.5 mol) of 47% hydrobromic acid was heated under reflux at 130° C. for 7 hours. After addition of distilled water, the mixture was concentrated under a reduced pressure to obtain 10.60 g (50 mmol) of 1,2,3,4-tetrahydro-6-hydroxynaphthalene-2-carboxylic acid.

THIRD STAGE

A mixture of 10.60 g (50 mmol) of the 1,2,3,4-tetrahydro-6-hydroxynaphthalene-2-carboxylic acid obtained in the second stage, 12.85 g (75 mmol) of benzyl bromide, 6.6 g (100 mmol) of 85% potassium hydroxide, 0.525 g (3.5 mmol) of sodium iodide, 200 ml of ethanol and 25 ml of distilled water was heated under reflux at 100° C. for 12 hours. To the mixture was added 50 ml of 10% potassium hydroxide, and they were further heated under reflux for 2 hours.

The reaction system was cooled to room temperature, and the reaction product was added to cold water. To the reaction mixture was added 36% hydrochloric acid to make the mixture acidic.

The mixture was filtered to obtain a precipitate, and the precipitate was recrystallized with toluene to obtain 13.08 g (46.4 mmol) of 1,2,3,4-tetrahydro-6-benzyloxynaphthalene-2-carboxylic acid.

FOURTH STAGE

To a mixture of 8.46 g (30 mmol) of the 1,2,3,4-tetrahydro-6-benzyloxynaphthalene-2-carboxylic acid obtained in the third stage, 5.52 g (30 mmol) of R-1-trifluoromethylheptanol, 0.37 g (3 mmol) of 4-N,N -dimethylaminopyridine and 80 ml of methylene chloride was dropwise added 30 ml of a methylene chloride solution containing 6.80 g (33 mmol) of N,N'-dicyclohexylcarbodiimide over 2.5 hours with stirring at room temperature.

Further, the reaction was carried out at room temperature for 15 hours.

The reaction mixture was filtered, and the filtrate obtained was concentrated. The resulting concentrate was separated by means of column chromatography to obtain 12.11 g (27.03 mmol) of 1,2,3,4-tetrahydro-6-benzyloxy-2-naphthalenecarboxylic acid R-1'-trifluoromethylheptyl ester as a light yellow transparent liquid.

FIFTH STAGE

Into a mixture of 12.11 g (27.03 mmol) of the 1,2,3,4-tetrahydro-6-benzyloxy-2-naphthalenecarboxylic acid R-1'-trifluoromethylheptyl ester obtained in the fourth stage, 1.21 g of 5% palladium/carbon catalyst and 80 ml of tetrahydrofuran was blown hydrogen gas for 48 hours with stirring at room temperature under normal pressure.

Subsequently, the reaction mixture was filtered using Celite as a filter aid, and the filtrate obtained was concentrated to obtain 9.65 g (26.95 mmol) of 1,2,3,4-tetrahydro-6-hydroxy-2-naphthalenecarboxylic acid R-1'-trifluoromethylheptyl ester as a light yellow liquid.

SIXTH STAGE

To a mixture of 0.36 g (1 mmol) of the 1,2,3,4-tetrahydro-6-hydroxy-2-naphthalenecarboxylic acid R-1'-trifluoromethylheptyl ester obtained in the fifth stage, 0.37 g (1 mmol) of 4-nonanoyloxybenzoic acid separately synthesized by a conventional process, 0.02 g (0.16 mmol) of 4-N,N-dimethylaminopyridine and 15 ml of methylene chloride was dropwise added 3 ml of a methylene chloride solution containing 0.25 g (1.2 mmol) of N,N'-dicyclohexylcarbodiimide over 2 hours with stirring at room temperature.

Further, the reaction was carried out at room temperature for 18 hours.

The reaction mixture was filtered, and the filtrate obtained was concentrated. The resulting concentrate was separated by means of column chromatography to obtain 0.45 g of a colorless semisolid.

This semisolid had a M/e value in FD-mass spectrum of 752.

A $^1$H-NMR spectrum of this compound is shown in FIG. 1.

From the analysis of the $^1$H-NMR spectrum, this compound was identified as 6-(4'-decanoyloxybiphenyl-4''-carbonyloxy)-1,2,3,4-tetrahydronaphthalene-2-carboxylic acid R-1'''-trifluoromethylheptyl ester [Exemplified Compound (3)].

EXAMPLE 2

Synthesis of 4-[4'-(6''-decanoyloxy -1'',2'',3'',4''-tetrahydro-2''-naphthoyloxy)benzoyloxy]benzoic acid R-1'''-trifluoromethylheptyl ester [Exemplified Compound (31)]

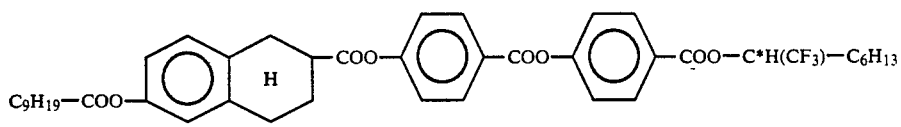

[31]

FIRST STAGE

To a mixture of 9.12 g (40 mmol) of 4-benzyloxybenzoic acid, 7.36 g (40 mmol) of R-1-trifluoromethylheptanol, 0.49 g (4 mmol) of 4-N,N-dimethylaminopyridine and 200 ml of methylene chloride was dropwise added 43 ml of a methylene chloride solution containing 9.06 g (44 mmol) of N,N'-dicyclohexylcarbodiimide over 1 hour with stirring at room temperature.

Further, the reaction was carried out at room temperature for 7 hours.

The reaction mixture was filtered, and the filtrate obtained was concentrated. The resulting concentrate was separated by means of column chromatography to obtain 12.00 g (30.1 mmol) of 4-benzyloxybenzoic acid R-1'-trifluoromethylheptyl ester as a colorless liquid.

SECOND STAGE

Into a mixture of 12.00 g (30.1 mmol) of the 4-benzyloxybenzoic acid R-1'-trifluoromethylheptyl ester obtained in the first stage, 2.4 g of 5% palladium/carbon catalyst and 50 ml of tetrahydrofuran was blown hydrogen gas for 19 hours with stirring at room temperature under normal pressure. The reaction mixture was filtered using Celite as a filter aid, and the filtrate obtained was concentrated to obtain 9.12 g (30.0 mmol) of 4-hydroxybenzoic acid R-1'-trifluoromethylheptyl ester as a light yellow transparent liquid.

THIRD STAGE

To a mixture of 1.52 g (5 mmol) of the 4-hydroxybenzoic acid R-1'-trifluoromethylheptyl ester obtained in the second stage, 1.14 g (5 mmol) of 4-benzyloxybenzoic acid, 0.06 g (0.5 mmol) of 4-N,N -dimethylaminopyridine and 30 ml of methylene chloride was dropwise added 5 ml of a methylene chloride solution containing 1.03 g (5 mmol) of N,N'-dicyclohexylcarbodiimide over 1.5 hours with stirring at room temperature.

Further, the reaction was carried out at room temperature for 6.5 hours.

The reaction mixture was filtered, and the filtrate obtained was concentrated. The resulting concentrate was separated by means of column chromatography to obtain 2.06 g (4.0 mmol) of 4-(4'-benzyloxy-benzoyloxy)benzoic acid R-1''-trifluoromethylheptyl ester as a white solid.

FOURTH STAGE

Into a mixture of 2.06 g (4.0 mmol) of the 4-(4'-benzyloxy-benzoyloxy)benzoic acid R-1''-trifluoromethylheptyl ester obtained in the third stage, 1.0 g of 5% palladium/carbon catalyst and 20 ml of tetrahydrofuran was blown hydrogen gas for 7.5 hours with stirring at room temperature under normal pressure. The reaction mixture was filtered using Celite as a filter aid, and the filtrate obtained was concentrated to obtain 1.70 g (4.0 mmol) of 4-(4'-hydroxy-benzoyloxy)benzoic acid R-1''-trifluoromethylheptyl ester as a white solid.

FIFTH STAGE

To a mixture of 0.59 g (1.4 mmol) of the 4-(4'-hydroxy-benzoyloxy)benzoic acid R-1''-trifluoromethylheptyl ester obtained in the fourth stage, 0.40 g (1.4 mmol) of the 1,2,3,4-tetrahydro-6-benzyloxynaphthalene-2-carboxylic acid obtained in the third stage of Example 1, 0.03 g (0.25 mmol) of 4-N,N-dimethylaminopyridine and 20 ml of methylene chloride was dropwise added 3 ml of a methylene chloride solution containing 0.37 g (1.8 mmol) of N,N'-dicyclohexylcarbodiimide over 1 hour with stirring at room temperature.

Further, the reaction was carried out at room temperature for 4 hours.

The reaction mixture was filtered, and the filtrate obtained was concentrated. The resulting concentrate was separated by means of column chromatography to obtain 0.82 g (1.2 mmol) of 4-[4'-(6''-benzyloxy-1'',2'',3'',4''-tetrahydro-2''-naphthoyloxy)benzoyloxy]benzoic acid R-1'''-trifluoromethylheptyl ester as a white solid.

SIXTH STAGE

Into a mixture of 0.82 g (1.2 mmol) of the 4-[4'-(6''-benzyloxy-1'',2'',3'',4''-tetrahydro-2''-naphthoyloxy)-benzoyloxy]benzoic acid R-1'''-trifluoromethylheptyl ester obtained in the fifth stage, 0.40 g of 5% palladium/carbon catalyst and 10 ml of tetrahydrofuran was blown hydrogen gas for 16 hours with stirring at room temperature under normal pressure. The reaction mixture was filtered using Celite as a filter aid, and the filtrate obtained was concentrated to obtain 0.69 g (1.15 mmol) of 4-[4'-(6''-hydroxy-1'',2'',3'',4''-tetrahydro-2''-naphthoyloxy)benzoyloxy]benzoic acid R-1'''-trifluoromethylheptyl ester as a white solid.

SEVENTH STAGE

To a mixture of 0.69 g (1.15 mmol) of the 4-[4'-(6''-hydroxy-1'',2'',3'',4''-tetrahydro-2''-naphthoyloxy)benzoyloxy]benzoic acid R-1'''-trifluoromethylheptyl ester obtained in the sixth stage, 0.21 g (1.22 mmol) of decanoic acid, 0.02 g (0.16 mmol) of 4-N,N-dimethylaminopyridine and 20 ml of methylene chloride was dropwise added 3 ml of a methylene chloride solution containing 0.31 g (1.5 mmol) of N,N'-dicyclohexylcarbodiimide over 1 hour with stirring at room temperature.

Further, the reaction was carried out at room temperature for 1 hour.

The reaction mixture was filtered, and the filtrate obtained was concentrated. The resulting concentrate was separated by means of column chromatography to obtain 0.63 g of a colorless semisolid.

This semisolid had a M/e value in FD-mass spectrum of 708.

A $^1$H-NMR spectrum of this compound is shown in FIG. 2.

From the analysis of the $^1$H-NMR spectrum, this compound was identified as 4-[4'-(6''-decanoyloxy-1'',2'',3'',4''-tetrahydro-2''-naphthoyloxy)benzoyloxy]-benzoic acid R-1'''-trifluoromethylheptyl ester [Exemplified Compound (31)].

EXAMPLE 3

The exemplified compound [31] represented by the following formula which was obtained in Example 2 and a compound [A] represented by the following formula were mixed in a mixing ratio of 50 : 50, to prepare a liquid crystal composition of the present invention.

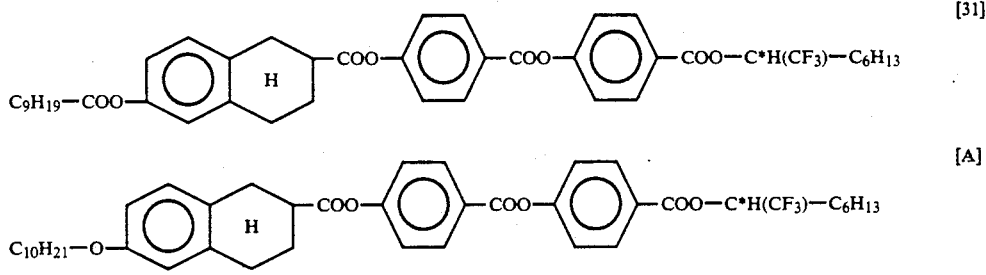

A phase transition temperature of the composition obtained as above was measured.

The result is set forth in Table 6, in which phase transition temperatures of the exemplified compound [31] and the compound [A] are also set forth.

TABLE 6

|  | Cry-SmC$_A$* | SmC$_A$*-SmA | SmA-Iso |
|---|---|---|---|
| [31] | 33° C. | 81° C. | 135° C. |
| [A] | 44° C. | 78° C. | 94° C. |
| [31](50%) + [A](50%) | < −30° C. | 56° C. | 113° C. |

Note:
In Table 6, [31] indicates the exemplified compound [31] and [A] indicates the compound [A].

EXAMPLE 4

The exemplified compound [31] represented by the following formula which was obtained in Example 2 and a compound [B] represented by the following formula were mixed in a mixing ratio of 90:10, to prepare a liquid crystal composition of the present invention.

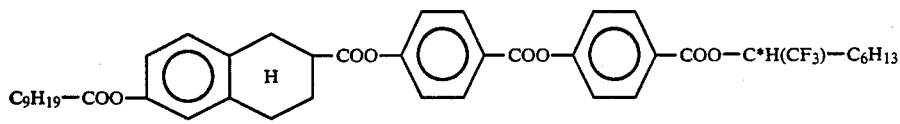

[31]

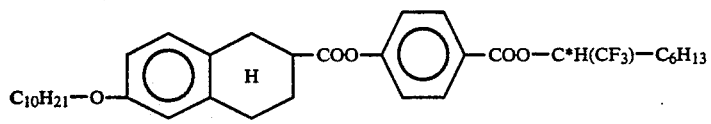

[B]

A phase transition temperature of the composition obtained as above was measured.

The result is set forth in Table 7, in which phase transition temperatures of the exemplified compound [31] and the compound [B] are also set forth.

TABLE 7

|  | Cry-SmC$_A$* or Iso | SmC$_A$*-SmA | SmA-Iso |
|---|---|---|---|
| [31] | 33° C. | 81° C. | 135° C. |
| [B] | 25° C. | — | — |
| [31](90%) + [B](10%) | 30° C. | 66° C. | 99° C. |

Note:
In Table 7, [31] indicates the exemplified compound [31] and [B] indicates the compound [B].

EXAMPLE 5

The exemplified compound [31] represented by the following formula which was obtained in Example 2 and a compound [C] represented by the following formula were mixed in a mixing ratio of 25:75, to prepare a liquid crystal composition of the present invention.

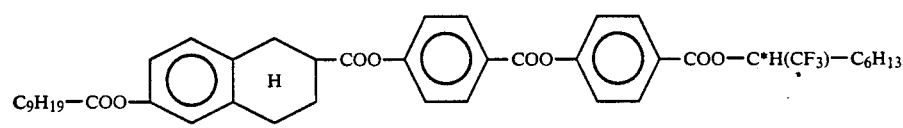

[31]

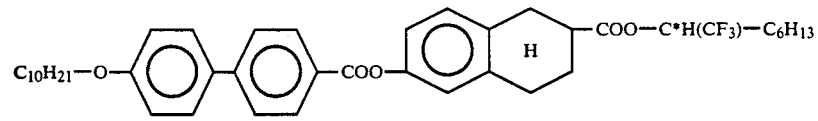

[C]

A phase transition temperature of the composition obtained as above was measured.

The result is set forth in Table 8, in which phase transition temperatures of the exemplified compound [31] and the compound [C] are also set forth.

TABLE 8

|  | Cry-SmC$_A$* | SmC$_A$*-SmA | SmA-Iso |
|---|---|---|---|
| [31] | 33° C. | 81° C. | 135° C. |
| [C] | 25° C. | 99° C. | 130° C. |
| [31](25%) + [C](75%) | <−30° C. | 87° C. | 126° C. |

Note:
In Table 8, [31] iindicates the exemplified compound [31] and [C] indicates the compound [C].

We claim:

1. A carboxylic acid ester compound represented by the following formula (I):

$$R-COO-A^1-Y^1-A^2-(Y^2-A^3)_n-COO-\overset{Q^1}{\underset{|}{C^*H}}-(CH_2)_q-CH_3 \quad (I)$$

wherein R is an alkyl group of 3-20 carbon atoms, n is 0 or 1, at least one of $A^1$ and $A^2$ is

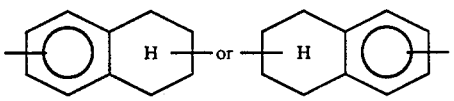

and the residual $A^1$, $A^2$ and $A^3$ are each independently

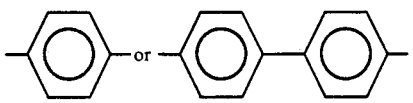

$Y^1$ and $Y^2$ are each —COO—, $Q^1$ is —CF$_3$, and q is an integer of 4 to 12.

2. The compound as claimed in claim 1 wherein $A^1$ is

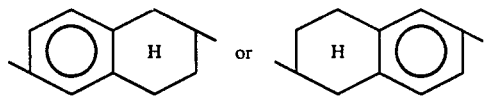

$A^2$ is

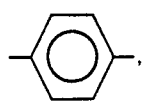

$Y^1$ is —COO—, $Q^1$ is —CF$_3$ and n is 0.

3. The compound as claimed in claim 1 wherein $A^1$ is

$A^2$ is

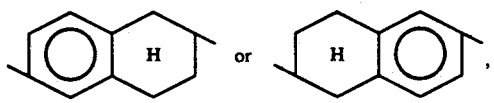

$Y^1$ is —COO—, $Q^1$ is —CF$_3$ and n is 0.

4. A liquid crystal material comprising a carboxylic acid ester compound represented by the following formula (I):

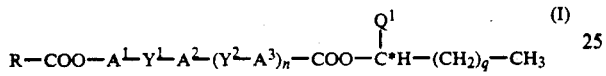

wherein R is an alkyl group of 3-20 carbon atoms, n is 0 or 1, at least one of $A^1$ and $A^2$ is

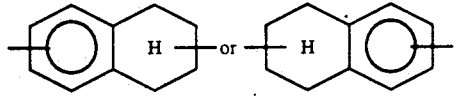

and the residual $A^1$, $A^2$ and $A^3$ are each independently

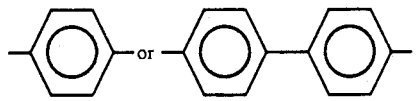

$Y^1$ and $Y^2$ are each —COO—, $Q^1$ is —CF$_3$, and q is an integer of 4 to 12.

5. A liquid crystal composition comprising at least two liquid crystal compounds, wherein at least one compound is a carboxylic acid ester compound represented by the following formula (I):

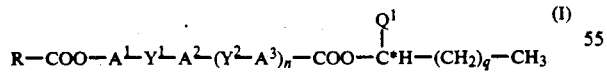

wherein R is an alkyl group of 3-20 carbon atoms, n is 0 or 1, at least one of $A^1$ and $A^2$ is

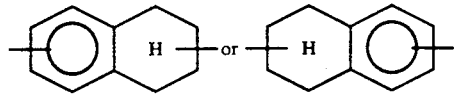

and the residual $A^1$, $A^2$ and $A^3$ are each independently

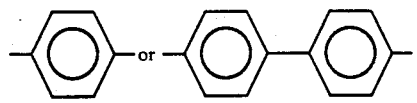

$Y^1$ and $Y^2$ are each —COO—, $Q^1$ is —CF$_3$, and q is an integer of 4 to 12.

6. A liquid crystal element comprising a cell and a liquid crystal material, said cell comprising two substrates facing each other and a gap formed by the substrates, said liquid crystal material being filed in the gap, in which the liquid crystal material comprises a carboxylic acid ester compound represented by the following formula (I):

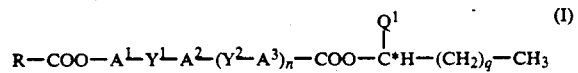

wherein R is an alkyl group of 3-20 carbon atoms, n is 0 or 1, at least one of $A^1$ and $A^2$ is

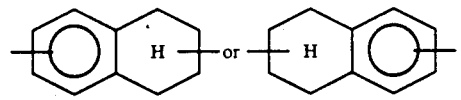

and the residual $A^1$, $A^2$ and $A^3$ are each independently

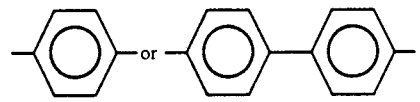

$Y^1$ and $Y^2$ are each —COO—, $Q^1$ is —CF$_3$, and q is an integer of 4 to 12.

7. A liquid cristal element comprising a cell and a liquid crystal composition, said cell comprising two substrates facing each other and a gap formed by the substrates, said liquid crystal composition being filled in the gap, in which the liquid crystal composition comprises at least two liquid crystal compounds, wherein at least one compound is a carboxylic acid ester compound represented by the following formula:

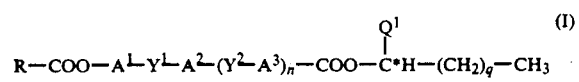

wherein R is an alkyl group of 3-20 carbon atoms, n is 0 or 1, at least one of $A^1$ and $A^2$ is

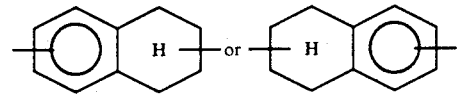

and the residual $A^1$, $A^2$ and $A^3$ are each independently

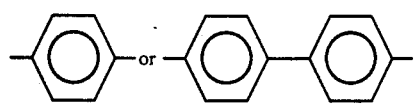
$Y^1$ and $Y^2$ are each —COO—, $Q^1$ is —CF$_3$, and q is an integer of 4 to 12.
8. A carboxylic acid ester compound as claimed in claim 1 represented by the following formula:
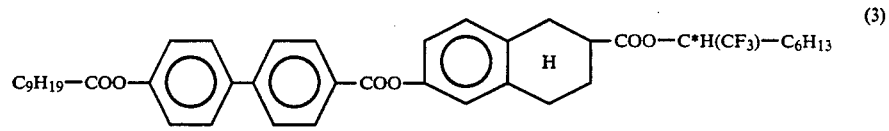
(3)
9. A carboxylic acid ester compound as claimed in claim 1 represented by the following formula:
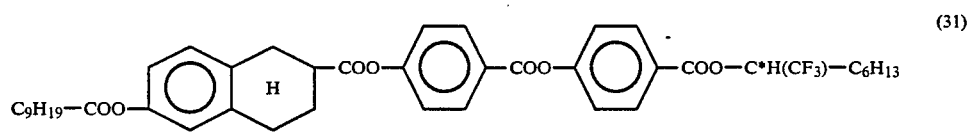
(31)
* * * * *